US009856288B2

(12) United States Patent
Hu et al.

(10) Patent No.: US 9,856,288 B2
(45) Date of Patent: Jan. 2, 2018

(54) TRIPEPTIDE EPOXYKETONE COMPOUND CONSTRUCTED BY HETEROCYCLE AND PREPARATION METHOD AND USE THEREOF

(71) Applicants: ZHEJIANG UNIVERSITY, Zhejiang (CN); SHANGHAI INSTITUTE OF MATERIA MEDICA, CHINESE ACADEMY OF SCIENCE, Shanghai (CN)

(72) Inventors: Yongzhou Hu, Zhejiang (CN); Jia Li, Shanghai (CN); Tao Liu, Zhejiang (CN); Jiankang Zhang, Zhejiang (CN); Yubo Zhou, Shanghai (CN); Bo Yang, Zhejiang (CN); Qiaojun He, Zhejiang (CN); Lei Xu, Shanghai (CN); Xiaobei Hu, Zhejiang (CN)

(73) Assignees: ZHEJIANG UNIVERSITY, Zhejiang (CN); SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 15/301,081

(22) PCT Filed: Mar. 11, 2015

(86) PCT No.: PCT/CN2015/073989
§ 371 (c)(1),
(2) Date: Sep. 30, 2016

(87) PCT Pub. No.: WO2015/149607
PCT Pub. Date: Oct. 8, 2015

(65) Prior Publication Data
US 2017/0022250 A1 Jan. 26, 2017

(30) Foreign Application Priority Data
Mar. 30, 2014 (CN) .......................... 2014 1 0122313

(51) Int. Cl.
*C07K 5/087* (2006.01)
*C07K 5/083* (2006.01)
*A61K 38/00* (2006.01)

(52) U.S. Cl.
CPC .......... *C07K 5/0812* (2013.01); *C07K 5/0808* (2013.01); *A61K 38/00* (2013.01); *Y02P 20/55* (2015.11)

(58) Field of Classification Search
None
See application file for complete search history.

(56) References Cited

U.S. PATENT DOCUMENTS 9,051,353 B2 * 6/2015 Phiasivongsa ....... C07D 417/12
2012/0214732 A1 * 8/2012 Kisselev ............ C07K 5/06043
514/4.6

FOREIGN PATENT DOCUMENTS

| CN | 102428075 | * | 10/2013 |
| CN | 103360348 | A | 10/2013 |
| WO | WO 9213549 | * | 8/1992 |
| WO | 2007/056464 | A1 | 5/2007 |
| WO | WO 2013/169282 | A1 | 11/2013 |
| WO | WO 2013169282 | A1 * | 11/2013 |
| WO | WO 2015149607 | * | 10/2015 |

OTHER PUBLICATIONS

Lv Juan, QSAR and Molecular Design Studies of Proteasome Inhibitors, Medical, health, and science and technology series of china masters' theses full-text database, Mar. 15, 2013 (Mar. 15, 2013), No. 3, ISSN 1674-0246.*
Arastu-Kapur S. et al., "Nonproteasomal Targets of the Proteasome Inhibitors Bortezomib and Carfilzomib: a Link to Clinical Adverse Events", *Clinical Cancer Research* 17(9):2734-2743 (May 1, 2011).
Jemal A. et al., "Global Cancer Statistics", *CA: A Cancer Journal for Clinicians* 61(2):69-90 (Mar./Apr. 2011).
Lv J., "QSAR and Molecular Design Studies of Proteasome Inhibitors", *Chinese Master's These Full-Text Database Medicine and Health Science 3* (113 pages) (Mar. 15, 2013), together with an English-language abstract.
Stewart B.W. et al., "World Cancer Report", *International Agency for Research on Cancer, World Health Organization* (pages) (2014).
International Search Report dated Jun. 17, 2015 received from International Application No. PCT/CN2015/073989.
Zhou, H. et al, "Design and Synthesis of an Orally Bioavailable and Selective Peptide Epoxyketone Proteasome Inhibitor (PR-047)", Journal of Medicinal Chemistry, vol. 52, No. 9, Apr. 6, 2009, pp. 3028-3038.
Dick, L. et al., "Building on bortezomib: second-generation proteasome inhibitors as anti-cancer therapy", Drug Discovery Today, Elsevier, vol. 15, Nos. 5-6, Mar. 1, 2010, pp. 243-249.
Chauhan, D. et al., "A novel orally active proteasome inhibitor ONX 0912 triggers in vitro and in vivo cytotoxicity in multiple myeloma", Blood, American Society of Hematology, vol. 116, No. 23, Dec. 2, 2010, pp. 4906-4915.
Extended European Search Report dated Oct. 24, 2017 received in European Patent Application No. 15773896.4.

* cited by examiner

*Primary Examiner* — Maury Audet
(74) *Attorney, Agent, or Firm* — Scully, Scott, Murphy & Presser, P.C.

(57) ABSTRACT

Disclosed are a tripeptide epoxyketone compound, a preparation method thereof, and a use thereof in the preparation of anti-tumor drugs.

18 Claims, 2 Drawing Sheets

TRIPEPTIDE EPOXYKETONE COMPOUND CONSTRUCTED BY HETEROCYCLE AND PREPARATION METHOD AND USE THEREOF

TECHNICAL FIELD

The present disclosure relates to the field of drug production, more specifically, to a novel class of tripeptide epoxy ketone compounds having a heterocycle in the peptide backbone, a preparation method thereof, and use of the above compounds in production of antitumor drugs.

BACKGROUND

With a continuous increase in the world population and on-going aging tendency of the population, and due to extensive existence of various unhealthy life-styles including smoking as well as the environmental pollution, tumors have been the first killer threatening the human health in the developed countries, and the second killer threatening the human health in the developing countries (CA-Cancer. J. Clin. 2011, 61, 69-90). In China, cancers have been the first cause of death. The World Health Organization (WHO) has published "Global Cancer Report 2014" On Feb. 3, 2014, stating that the newly increased cancer cases and death cases are in the highest level in the world. Conventional chemotherapeutic drugs, such as alkylating agents, antimetabolites, etc., generally have disadvantages of high toxic and side effect and liability to drug resistance. Meanwhile, antitumor drugs designed against key proteins or kinases in signaling pathways are playing more and more important role in the field of tumor treatment. Therefore, it is greatly important to develop novel antitumor drugs with high efficacy and low toxicity, which is vital to the people's livelihood.

Proteasome is a macromolecular complex having multiple subunits and broadly distributed in eukaryotic cytoplasms and nuclei. The Proteasome has various catalytic functions, regulating metabolism of 80%-90% of proteins in the cell, and being involved in the cell cycle regulation, cell apoptosis, cell signaling, DNA repairing and various physiological functions, thereby playing important roles in the growth and development of cells. The proteasome plays regulatory roles in various life processes by regulating the level of key proteins (such as, P53, NF-κB) influencing the cell signaling pathway. Meanwhile, many of those regulatory proteins (such as, cyclins) play important role in oncogenesis and growth of tumors. The proteasome inhibitor may affect degradation of various cyclins in the cell and promote cell apoptosis by inhibiting activity of the proteasome.

In the past decades, small molecular compounds of various structures have been found to have proteasome inhibitory activity and strong antitumor effect. Currently, two small molecular proteasome inhibitors have been used clinically, namely, Bortezomib as a compound of peptide borates and Carfilzomib as a compound of epoxy ketone peptides. This further confirms validity of the proteasome as the target of tumor treatment.

In comparison with Bortezomib, Carfilzomib as an epoxy ketone compound not only has good tumor inhibitory effect, but also has no toxic and side effect of causing neurological injury shared by common proteasome inhibitors. The reason for this may be that Carfilzomib has more specific proteasome inhibitory activity and significantly lower inhibitory activity for other proteases as compared with Bortezomib (Clin Cancer Res. 2011, 17, 2734-2743). Carfilzomib developed by Onyx Pharmaceuticals, Inc. (U.S.A.) has been approved by the Food and Drug Administration (FDA) through an accelerated procedure in 2012, which is mainly used for treating the patient of multiple myeloma who has received at least two therapies of higher precedence (including Bortezomib, the first generation of proteasome inhibitor, and an immunomodulator). In comparison with the first generation of proteasome inhibitor, Carfilzomib is significant advantageous in that it may overcome the resistances to conventional antitumor drugs and have better safety, which render the treatment of multiple myeloma more hopeful.

Using Carfilzomib as a lead compound, the present disclosure has designed and synthesized a series of novel small molecular short peptide-based proteasome inhibitors, structurally featured in a tripeptide epoxy ketone compound constructed with a heterocycle. Such compounds have been evaluated for their proteasome inhibitory activity at molecular, cellular and animal levels. Meanwhile, they have been investigated for their antitumor activity at a cellular level and at an animal level. The results have shown that such compounds have an extremely strong proteasome inhibitory activity and cell proliferation inhibitory activity as a promising proteasome inhibitor, and may provide a new insight into the research of drugs for treating cancers.

SUMMARY

The object of the present disclosure is to provide a novel tripeptide epoxy ketone compound constructed with a heterocycle having the following structural formula,

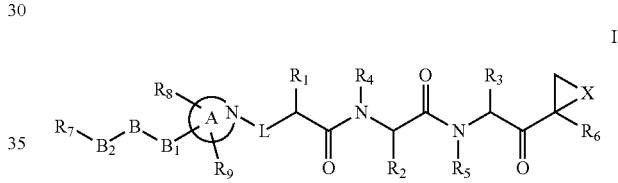

wherein:

$R_1$, $R_2$ and $R_3$ are each independently selected from the group consisting of H, $C_{1-6}$ alkyl-D, halogenated $C_{1-6}$ alkyl-D, $C_{1-6}$ hydroxy alkyl, $C_{1-6}$ mercapto alkyl, $C_{1-6}$ alkoxy alkyl, aryl, aralkyl, heteroaryl, heteroaralkyl, where D is $N(R_a)(R_b)$ or absent, $R_a$ and $R_b$ are each independently selected from the group consisting of H, OH, $C_{1-6}$ alkyl, halogenated $C_{1-6}$ alkyl and a protective group for the N-terminal;

$R_4$ and $R_5$ are each independently selected from the group consisting of H, OH, $C_{1-6}$ alkyl, halogenated $C_{1-6}$ alkyl, and aralkyl;

$R_6$ is selected from the group consisting of H, $C_{1-6}$ alkyl, halogenated $C_{1-6}$ alkyl, $C_{1-6}$ hydroxy alkyl, $C_{1-6}$ alkoxy group, halogenated $C_{1-6}$ alkoxy group, C(O)O—$C_{1-6}$ alkyl, C(O)NH—$C_{1-6}$ alkyl, and aralkyl;

X is O, S, NH, N—$C_{1-6}$ alkyl, N-halogenated $C_{1-6}$ alkyl;

L is

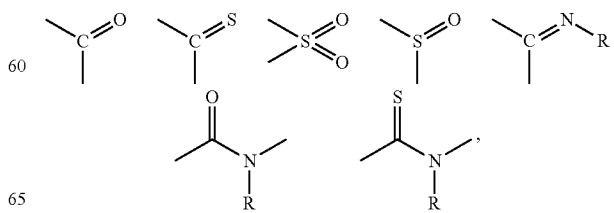

or is absent, where R is selected from the group consisting of H, $C_{1-6}$ alkyl and halogenated $C_{1-6}$ alkyl;

the ring A is selected from the group consisting of a 5-7 membered saturated aliphatic heterocycle, unsaturated heterocycle, and a substituted 5-7 membered saturated aliphatic heterocycle, unsaturated heterocycle, where the heterocycle contains 0-3 heteroatoms selected from the group consisting of O, N and S, and is optionally substituted by those selected from the group consisting of $R_8$, $R_9$ and $B_1$;

$R_8$ and $R_9$ are each independently selected from the group consisting of H, OH, $C_{1-6}$ alkyl, $C_{1-6}$ alkoxy group, $C_{1-6}$ hydroxy alkyl, $C_{1-6}$ mercapto alkyl, $C_{1-6}$ alkyl-D, aryl, heterocyclic aryl, cycloalkyl and heterocyclic group, which groups may be optionally substituted by those selected from the group consisting of halogen, nitro, amino, CN—, $C_{1-6}$ alkyl, halogenated $C_{1-6}$ alkyl, $C_{1-6}$ alkoxy group and halogenated $C_{1-6}$ alkoxy group, and each of which groups may be optionally fused to one or more aryl or heterocyclic aryl, or be fused to one or more saturated or partially unsaturated cycloalkyl or heterocycle;

$B_1$ and $B_2$ are the same or different, and are each independently selected from the group consisting of O, S, N($R_c$), C($R_d$)($R_e$) or are absent, where $R_c$, $R_d$ and $R_e$ are each independently selected from the group consisting of H, $C_{1-6}$ alkyl, halogenated $C_{1-6}$ alkyl, $C_{1-6}$ alkoxy group and halogenated $C_{1-6}$ alkoxy group, and $R_c$, $R_d$ and $R_e$ are the same or different;

B is selected from the group consisting of

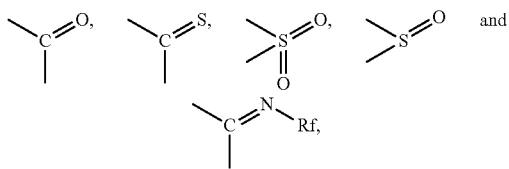

or is absent, where $R_f$ is selected from the group consisting of H, $C_{1-6}$ alkyl and halogenated $C_{1-6}$ alkyl;

$R_7$ is selected from the group consisting of H, $C_{1-6}$ alkyl, $C_{1-6}$ alkenyl, $C_{1-6}$ alkynyl, carbocyclic group, heterocyclic group, aryl, $C_{1-6}$ aralkyl, heteroaryl, $C_{1-6}$ heteroaralkyl, $R_g$-ZEZ—$C_{1-8}$ alkyl, $R_g$—ZEZ—$C_{1-8}$ alkyl-ZEZ—$C_{1-8}$ alkyl, heterocyclic group-MZEZ—$C_{1-8}$ alkyl, $(R_g)_2$N—$C_{1-8}$ alkyl, heterocyclic group-M-, carbocyclic group-M-, which groups may be optionally substituted by those selected from the group consisting of halogen, nitro, amino, CN—, $C_{1-6}$ alkyl, halogenated $C_{1-6}$ alkyl, $C_{1-6}$ alkoxy group and halogenated $C_{1-6}$ alkoxy group, where E is optionally a covalent bond if Z is present adjacently, M is absent or is a $C_{1-12}$ alkyl, and Z is optionally a covalent bond if E is present adjacently.

Preferably, X is O atom.
Preferably, L is

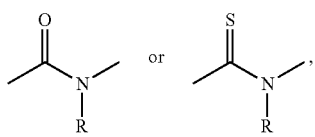

where R is H, $C_{1-6}$ alkyl or halogenated $C_{1-6}$ alkyl.

$B_1$ and $B_2$ are each independently preferably O, S, or N($R_c$), or are absent, and $R_c$ is selected from the group consisting of H, $C_{1-6}$ alkyl, halogenated $C_{1-6}$ alkyl, $C_{1-6}$ alkoxy group, halogenated $C_{1-6}$ alkoxy group.

Preferably, B is

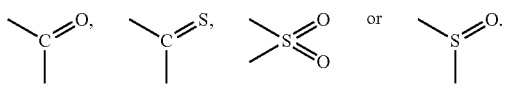

Preferably, the ring A is a six membered saturated aliphatic heterocycle or unsaturated heterocycle.

Preferably, the prevent disclosure provides the following compounds, wherein each of the mentioned amino acids is an L-amino acid, unless particularly specified.

4-(pyrazin-2-yl carbamoyl)piperidin-1-oyl-Phe-Leu-Leu-epoxy ketone (5a);
4-(pyrazin-2-yl carbamoyl)piperidin-1-oyl-Leu-Phe-Leu-epoxy ketone (5b);
4-(pyrazin-2-oyl)piperazin-1-oyl-Leu-Phe-Leu-epoxy ketone (5c);
4-(4-fluorophenyl carbamoyl)piperidin-1-oyl-Leu-Phe-Leu-epoxy ketone (5d);
4-(4-benzoyl phenyl carbamoyl)piperidin-1-oyl-Leu-Phe-Leu-epoxy ketone (5e);
4-(biphenyl-4-yl carbamoyl)piperidin-1-oyl-Leu-Phe-Leu-epoxy ketone (5f);
4-(4-chlorophenyl carbamoyl)piperidin-1-oyl-Leu-Phe-Leu-epoxy ketone (5g);
4-(4-methoxy phenyl carbamoyl)piperidin-1-oyl-Leu-Phe-Leu-epoxy ketone (5h);
4-(isoxazol-3-yl carbamoyl)piperidin-1-oyl-Leu-Phe-Leu-epoxy ketone (5i);
4-(thiazol-2-yl carbamoyl)piperidin-1-oyl-Leu-Phe-Leu-epoxy ketone (5j);
4-(pyridin-2-yl carbamoyl)piperidin-1-oyl-Leu-Phe-Leu-epoxy ketone (5k);
4-(pyridin-3-yl carbamoyl)piperidin-1-oyl-Leu-Phe-Leu-epoxy ketone (5l);
4-(4-chlorophenyl carbamoyl)piperazin-1-oyl-Leu-Phe-Leu-epoxy ketone (5m);
4-(4-methoxy phenyl carbamoyl)piperazin-1-oyl-Leu-Phe-Leu-epoxy ketone (5n);
4-(4-chloro benzamido)piperidin-1-oyl-Leu-Phe-Leu-epoxy ketone (5o);
4-(4-methoxy benzamido)piperidin-1-oyl-Leu-Phe-Leu-epoxy ketone (5p);
4-(morpholin-4-oyl)piperidin-1-oyl-Leu-Phe-Leu-epoxy ketone (5q);
3-(pyrazin-2-yl carbamoyl)piperidin-1-oyl-Leu-Phe-Leu-epoxy ketone (5r);
3-(4-chlorophenyl carbamoyl)piperidin-1-oyl-Leu-Phe-Leu-epoxy ketone (5s);
4-(pyrazin-2-yl carbamoyl)piperidin-1-oyl-Leu-Phe-Leu-cyclothione (5t);
4-(4-fluorophenyl carbamoyl)piperidin-1-oyl-Leu-Phe-Leu-cyclothione (5u);
4-(pyrazin-2-yl carbamoyl)piperidin-1-oyl-Leu-Phe-Leu-aziridinone (5v); or
4-(pyrazin-2-yl carbamoyl)piperidin-1-oyl-Leu-Phe-Leu-(N-ethyl aziridinone) (5w).

Another object of the present disclosure is to provide a method for preparing the above compounds, comprising the steps of:

(1) reacting a compound 6 with a protected amino acid for 2-8 h under the action of a condensing agent at a reaction temperature of 0-50° C. to give a compound 7 as a crude product to be used directly in the next step, wherein the condensing agent is selected from the group consisting of dicyclohexyl carbodiimide/4-dimethyl amino pyridine, dicyclohexyl carbodiimide/1-hydroxy benzotriazole, and N-(3-dimethyl amino propyl)-N'-ethyl carbodiimide hydrochloride/1-hydroxy benzotriazole, (2) deprotecting the Boc protective group off the compound 7 for 0.5-3 h in an acidic condition at a reaction temperature of −10 to 40° C. to give a crude product to be used directly in the next step, wherein the acidic condition is in the presence of a solution of HCl in ether, a solution of HCl in ethyl acetate, a solution of HCl in methanol, a solution of HCl in dioxane, or trifluoroacetic acid, (3) deprotecting the Boc protective group off the compound 1 in an acidic condition same as the reaction condition in the step of (2) to give a compound 2 as a crude product to be used directly in the next step, (4) reacting an amino acid methyl ester with triphosgene for 10 min to 1 h in a basic condition in the presence of sodium carbonate, sodium bicarbonate, triethylamine or diisopropylethylamine at a reaction temperature of −20 to 0° C. to give amino acid methyl ester isocyanate, and condensing the isocyanate with the compound 2 in a basic condition in the presence of triethylamine or diisopropyl ethylamine at a reaction temperature of 0-50° C. for 1-6 h to give a compound 3 as a crude product to be used directly in the next step, (5) hydrolyzing the compound 3 in a basic condition in the presence of sodium hydroxide, lithium hydroxide or potassium hydroxide under a reaction temperature of 0-40° C. for 0.5-2 h to give a compound 4 as a product to be used directly in the next step, (6) reacting the compound 4 with a compound 8 under the action of the same condensing agent as that in the step of (1) to give a product 5, and isolating the resultant crude product through column chromatography to give a pure product, Reaction Scheme:

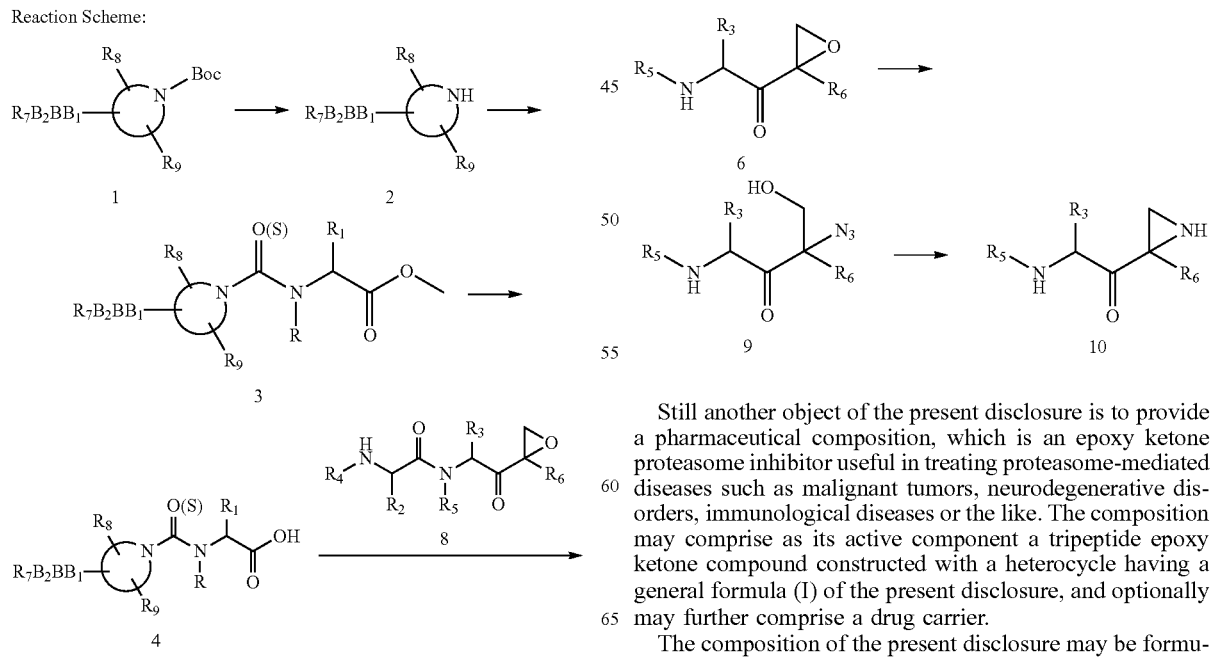

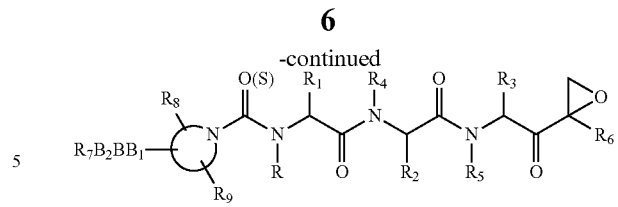

The compound 8 as a raw material may be prepared according to the following scheme:

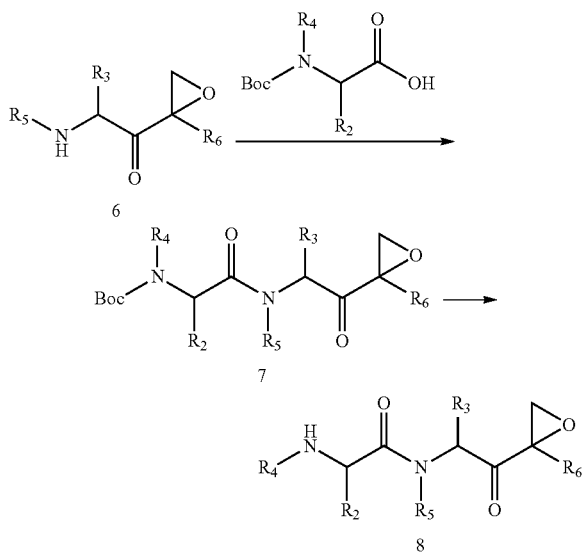

Synthesis of the compound 6 as a raw material can be found in *J. Med. Chem.* 2009, 52, 3028.

The compound 10 used as a raw material for preparation of the compound containing aziridinone can be prepared according to the following scheme:

Still another object of the present disclosure is to provide a pharmaceutical composition, which is an epoxy ketone proteasome inhibitor useful in treating proteasome-mediated diseases such as malignant tumors, neurodegenerative disorders, immunological diseases or the like. The composition may comprise as its active component a tripeptide epoxy ketone compound constructed with a heterocycle having a general formula (I) of the present disclosure, and optionally may further comprise a drug carrier.

The composition of the present disclosure may be formulated into various pharmaceutical dosage forms for, e.g., oral, injection, inhalation and implantation administrations. The injection and oral administrations are preferred as, e.g., injections, freeze-dried powder injections, tablets, capsules, granulates or the like.

The pharmaceutical composition and various formulations thereof may be prepared by using conventional pharmaceutical carriers.

Still another object of the present disclosure is to provide pharmaceutical use of the compound of general formula (I) and the pharmaceutical composition comprising the compound. That is, the present disclosure provides the use of the compound of general formula (I) and the pharmaceutical composition comprising the compound in manufacture of drugs for treatment of malignant tumors, neurodegenerative disorders and immunological diseases.

It has been demonstrated experimentally that the present tripeptide epoxy ketone compounds constructed with a heterocycle has an excellent proteasome inhibitory activity, and shows an extremely strong proliferation inhibitory effect in vitro on cell strains of multiple myeloma and various other solid tumors, such as, RPMI8226, H929, MM-1R, MM-1S or the like. The present compounds may be synthesized with easily obtainable materials according to a rationally designed scheme in a mild reaction condition with a high yield in each of the steps. The synthesis can be performed by convenient operations, and is suitable for industrial production.

DETAILED DESCRIPTION OF THE INVENTION

Figure 1:
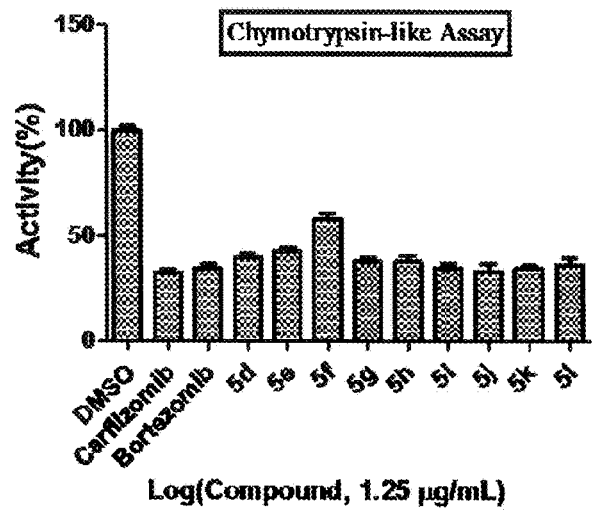
FIG. 1 shows the inhibitory activity of part of the compounds on the proteasome CT-L in hemocytes.

The present disclosure is further described in connection with the following Examples which are merely for the illustrative purpose, rather than limiting the present disclosure in any way.

Preparation Example 1. tert-butyl 4-(pyrazin-2-yl carbamoyl)piperidine-1-carboxylic acid ester (1a, 1b)

1-(tert-butoxy carbonyl)piperidine-4-carboxylic acid (2.75 g, 12 mmol) was placed in a 50 mL three-necked flask. 25 mL anhydrous $CH_2Cl_2$ was added under the protection of $N_2$, and then pyridine (2.5 mL, 30 mmol) and dichlorosulfoxide (1.1 mL, 14 mmol) were added dropwise slowly. The resultant reaction mixture was stranded at the room temperature for 0.5 h. Subsequently, 2-amino pyrazine (0.95 g, 10 mmol) and triethylamine (5.7 mL, 40 mmol) dissolved in 15 mL $CH_2Cl_2$ were added dropwise slowly to the reaction mixture. The reaction was carried out at the room temperature for 6 h. Thereafter, to the reaction mixture was added 20 mL saturated aqueous NaCl. The organic layer was separated and the aqueous layer was extracted with $CH_2Cl_2$ (15 mL*3). The organic layers were combined, dried over anhydrous $Na_2SO_4$, and evaporated under a reduced pressure to remove the solvent. The resultant product was subjected to column chromatography to give 2.3 g of white solid with the yield of 74%. m.p.: 134-136° C.; $^1H$ NMR (500 MHz, $CDCl_3$): δ=9.55 (s, 1H, pyrazine-H), 8.35 (d, 1H, J=2.0 Hz, pyrazine-H), 8.23 (s, 1H, pyrazine-H), 7.97 (s, 1H, NH), 4.20 (m, 2H, $CH_2$), 2.81 (m, 2H, $CH_2$), 2.48 (m, 1H, CH), 1.93 (d, 2H, J=12.5 Hz, $CH_2$), 1.76 (m, 2H, $CH_2$), 1.47 (s, 9H, $CH_3$) ppm; ESI-MS: m/z=307 $[M+H]^+$.

Preparation Example 2. tert-butyl 4-(pyrazin-2-oyl)piperazine-1-carboxylic acid ester (1c)

Pyrazine-2-carboxylic acid (1.5 g, 12 mmol) was placed in a 50 mL reaction flask. After 35 mL anhydrous $CH_2Cl_2$ was added to dissolve pyrazine-2-carboxylic acid, 1-hydroxy benzotriazole (1.6 g, 12 mmol) and N-(3-dimethyl-aminopropyl)-N'-ethylcarbodiimide hydrochloride (3.5 g, 18 mmol) were added. The reaction was carried out at the room temperature for half a hour. Subsequently, tert-butyl piperazine-1-carboxylic acid ester (1.9 g, 10 mmol) was added to the reaction mixture. The reaction was carried out for an additional 3 h at the room temperature. Thereafter, to the reaction mixture was added 30 mL saturated aqueous $NaHCO_3$ solution. The organic layer was separated and washed with saturated aqueous NaCl (20 mL*2), dried over anhydrous $Na_2SO_4$, and evaporated under a reduced pressure to remove the solvent. The resultant product was subjected to column chromatography to give 2.4 g of white solid with the yield of 83%. m.p.: 146-148° C.; $^1H$ NMR (500 MHz, $CDCl_3$): δ=8.97 (d, 1H, J=1.5 Hz, pyrazine-H), 8.65 (d, 1H, J=2.5 Hz, pyrazine-H), 8.54 (s, 1H, pyrazine-H), 3.79 (t, 2H, J=5.0 Hz, $CH_2$), 3.62 (t, 2H, J=5.0 Hz, $CH_2$), 3.56 (t, 2H, J=5.0 Hz, $CH_2$), 3.49 (t, 2H, J=5.0 Hz, $CH_2$), 1.47 (s, 9H, $CH_3$) ppm; ESI-MS: m/z=293 $[M+H]^+$.

Preparation Example 3. tert-butyl 4-(4-fluorophenyl carbamoyl)piperidine-1-carboxylic acid ester (1d)

By using 4-fluoro aniline as a raw material, the synthesis and post-treatment were carried out according to the same procedure as in Preparation Example 1. 2.4 g of white solid was obtained with the yield of 75%. m.p.: 147-149° C.; $^1H$ NMR (500 MHz, $CDCl_3$): δ=7.47 (m, 2H, Ar—H), 7.20 (s, 1H, NH), 7.01 (t, 2H, J=8.0 Hz, Ar—H), 4.18 (d, 2H, J=12.0 Hz, $CH_2$), 2.80 (t, 2H, J=12.5 Hz, $CH_2$), 2.37 (m, 1H, CH), 1.90 (d, 2H, J=12.5 Hz, $CH_2$), 1.75 (m, 2H, $CH_2$), 1.47 (s, 9H, $CH_3$) ppm; ESI-MS: m/z=323 $[M+H]^+$.

Preparation Example 4. tert-butyl 4-(4-benzoyl phenyl carbamoyl)piperidine-1-carboxylic acid ester (1e)

By using (4-amino phenyl)benzophenone as a raw material, the synthesis and post-treatment were carried out according to the same procedure as in Preparation Example 1. 3.0 g of white solid was obtained with the yield of 73%. m.p.: 162-164° C.; $^1H$ NMR (500 MHz, $CDCl_3$): δ=7.82 (d, 2H, J=8.5 Hz, Ar—H), 7.77 (d, 2H, J=8.5 Hz, Ar—H), 7.67 (d, 2H, J=9.5 Hz, Ar—H), 7.58 (t, 1H, J=7.0 Hz, Ar—H), 7.48 (t, 2H, J=8.0 Hz, Ar—H), 7.41 (s, 1H, NH), 4.18 (d, 2H, J=12.5 Hz, $CH_2$), 2.78 (t, 2H, J=13.0 Hz, $CH_2$), 2.44 (m, 1H, CH), 1.90 (d, 2H, J=11.5 Hz, $CH_2$), 1.77 (m, 2H, $CH_2$), 1.48 (s, 9H, $CH_3$) ppm; ESI-MS: m/z=409 $[M+H]^+$.

Preparation Example 5. tert-butyl 4-(biphenyl-4-yl carbamoyl)piperidine-1-carboxylic acid ester (1f)

By using 4-amino biphenyl as a raw material, the synthesis and post-treatment were carried out according to the same procedure as in Preparation Example 1. 2.3 g of white solid was obtained with the yield of 60%. m.p.: 219-221° C.; $^1$H NMR (500 MHz, CDCl$_3$): δ=7.57 (m, 6H, Ar—H), 7.43 (t, 2H, J=7.5 Hz, Ar—H), 7.33 (t, 1H, J=7.5 Hz, Ar—H), 7.22 (s, 1H, NH), 4.20 (d, 2H, J=12.5 Hz, CH$_2$), 2.81 (t, 2H, J=12.0 Hz, CH$_2$), 2.40 (m, 1H, CH), 1.93 (d, 2H, J=11.5 Hz, CH$_2$), 1.76 (m, 2H, CH$_2$), 1.47 (s, 9H, CH$_3$) ppm; ESI-MS: m/z=381 [M+H]$^+$.

Preparation Example 6. tert-butyl 4-(4-chlorophenyl carbamoyl)piperidine-1-carboxylic acid ester (1g)

By using 4-chloro aniline as a raw material, the synthesis and post-treatment were carried out according to the same procedure as in Preparation Example 1. 3.3 g of white solid was obtained with the yield of 98%. m.p.: 187-189° C.; $^1$H NMR (500 MHz, CDCl$_3$): δ=7.47 (d, 2H, J=9.0 Hz, Ar—H), 7.42 (s, 1H, NH), 7.27 (d, 2H, J=7.5 Hz, Ar—H), 4.18 (d, 2H, J=13.5 Hz, CH$_2$), 2.77 (t, 2H, J=12.0 Hz, CH$_2$), 2.38 (m, 1H, CH), 1.88 (d, 2H, J=11.0 Hz, CH$_2$), 1.73 (m, 2H, CH$_2$), 1.47 (s, 9H, CH$_3$) ppm; ESI-MS: m/z=339 [M+H]$^+$.

Preparation Example 7. tert-butyl 4-(4-methoxy phenyl carbamoyl)piperidine-1-carboxylic acid ester (1h)

By using 4-methoxy aniline as a raw material, the synthesis and post-treatment were carried out according to the same procedure as in Preparation Example 1. 2.8 g of white solid was obtained with the yield of 85%. m.p.: 165-167° C.; $^1$H NMR (500 MHz, CDCl$_3$): δ=7.39 (d, 2H, J=8.5 Hz, Ar—H), 7.38 (s, 1H, NH), 6.83 (d, 2H, J=7.5 Hz, Ar—H), 4.16 (d, 2H, J=13.0 Hz, CH$_2$), 3.77 (s, 3H, CH$_3$), 2.75 (m, 2H, CH$_2$), 2.36 (m, 1H, CH), 1.86 (d, 2H, J=12.0 Hz, CH$_2$), 1.71 (m, 2H, CH$_2$), 1.45 (s, 9H, CH$_3$) ppm; ESI-MS: m/z=335 [M+H]$^+$.

Preparation Example 8. tert-butyl 4-(isoxazol-3-yl carbamoyl)piperidine-1-carboxylic acid ester (1i)

By using 3-amino isoxazole as a raw material, the synthesis and post-treatment were carried out according to the same procedure as in Preparation Example 1. 2.5 g of white solid was obtained with the yield of 84%. m.p.: 164-166° C.; $^1$H NMR (500 MHz, CDCl$_3$): δ=9.92 (s, 1H, NH), 8.35 (d, 1H, J=2.0 Hz, isoxazole-H), 7.24 (d, 1H, J=2.0 Hz, isoxazole-H), 4.10 (m, 2H, CH$_2$), 2.88 (m, 2H, CH$_2$), 2.62 (m, 1H, CH), 1.99 (d, 2H, J=11.0 Hz, CH$_2$), 1.83 (m, 2H, CH$_2$), 1.47 (s, 9H, CH$_3$) ppm; ESI-MS: m/z=296 [M+H]$^+$.

Preparation Example 9. tert-butyl 4-(thiazol-2-yl carbamoyl) piperidine-1-carboxylic acid ester (1j)

By using 2-amino thiazole as a raw material, the synthesis and post-treatment were carried out according to the same procedure as in Preparation Example 1. 2.5 g of white solid was obtained with the yield of 84%. m.p.: 192-194° C.; $^1$H NMR (500 MHz, CDCl$_3$): δ=12.10 (s, 1H, NH), 7.42 (d, 1H, J=4.0 Hz, thiazole-H), 7.05 (d, 1H, J=3.5 Hz, thiazole-H), 4.19 (m, 2H, CH$_2$), 2.86 (m, 2H, CH$_2$), 2.65 (m, 1H, CH), 1.91 (d, 2H, J=11.5 Hz, CH$_2$), 1.83 (m, 2H, CH$_2$), 1.48 (s, 9H, CH$_3$) ppm; ESI-MS: m/z=312 [M+H]$^+$.

Preparation Example 10. tert-butyl 4-(pyridin-2-yl carbamoyl)piperazine-1-carboxylic acid ester (1k)

By using 2-amino pyridine as a raw material, the synthesis and post-treatment were carried out according to the same procedure as in Preparation Example 1. 2.8 g of white solid was obtained with the yield of 92%. m.p.: 156-158° C.; $^1$H NMR (500 MHz, CDCl$_3$): δ=8.25 (m, 3H, pyridine-H+NH), 7.74 (m, 1H, pyridine-H), 7.06 (dd, 1H, J=6.5, 5.0 Hz, pyridine-H), 4.18 (m, 2H, CH$_2$), 2.79 (m, 2H, CH$_2$), 2.43 (m, 1H, CH), 1.91 (d, 2H, J=12.5 Hz, CH$_2$), 1.74 (m, 2H, CH$_2$), 1.46 (s, 9H, CH$_3$) ppm; ESI-MS: m/z=306 [M+H]$^+$.

Preparation Example 11. tert-butyl 4-(pyridin-3-yl carbamoyl) piperazine-1-carboxylic acid ester (1l)

By using 3-amino pyridine as a raw material, the synthesis and post-treatment were carried out according to the same procedure as in Preparation Example 1. 2.6 g of white solid was obtained with the yield of 86%. m.p.: 53-55° C.; $^1$H NMR (500 MHz, CDCl$_3$): δ=8.61 (s, 1H, pyridine-H), 8.34 (d, 1H, J=4.0 Hz, pyridine-H), 8.28 (d, 1H, J=8.5 Hz, pyridine-H), 7.81 (s, 1H, NH), 7.32 (dd, 1H, J=8.5, 5.0 Hz, pyridine-H), 4.19 (d, 2H, J=13.0 Hz, CH$_2$), 2.79 (m, 2H, CH$_2$), 2.50 (m, 1H, CH), 1.91 (d, 2H, J=12.0 Hz, CH$_2$), 1.75 (m, 2H, CH$_2$), 1.46 (s, 9H, CH$_3$) ppm; ESI-MS: m/z=306 [M+H]$^+$.

Preparation Example 12. tert-butyl 4-(4-chlorophenyl carbamoyl)piperazine-1-carboxylic acid ester (1m)

Tert-butyl piperazine-1-carboxylic acid ester (1.9 g, 10 mmol) dissolved in 30 mL anhydrous CH$_2$Cl$_2$ was cooled to 0° C. in an ice-bath. 4-chlorophenyl isocyanate (1.5 g, 10 mmol) dissolved in 10 mL anhydrous CH$_2$Cl$_2$ was dropped into the resultant mixture slowly. The reaction was carried out for 1 h at the room temperature. The resultant mixture was evaporated under a reduced pressure to remove the solvent. The obtained product was subjected to column chromatography to give 3.0 g white solid with the yield of 89%. m.p.: 147-149° C.; $^1$H NMR (500 MHz, CDCl$_3$): δ=7.27 (d, 2H, J=9.0 Hz, Ar—H), 7.19 (d, 2H, J=9.0 Hz, Ar—H), 6.79 (s, 1H, NH), 3.44 (s, 8H, CH$_2$), 1.46 (s, 9H, CH$_3$) ppm; ESI-MS: m/z=340 [M+H]$^+$.

Preparation Example 13. tert-butyl 4-(4-methoxy phenyl carbamoyl)piperazine-1-carboxylic acid ester (1n)

By using p-methoxy phenyl isocyanate as a raw material, the synthesis and post-treatment were carried out according to the same procedure as in Preparation Example 12. 2.9 g of white solid was obtained with the yield of 88%. m.p.: 174-176° C.; $^1$H NMR (500 MHz, CDCl$_3$): δ=7.22 (d, 2H, J=9.0 Hz, Ar—H), 6.82 (d, 2H, J=9.0 Hz, Ar—H), 6.42 (s, 1H, NH), 3.77 (s, 3H, CH$_3$), 3.45 (s, 8H, CH$_2$), 1.47 (s, 9H, CH$_3$) ppm; ESI-MS: m/z=336 [M+H]$^+$.

Preparation Example 14. tert-butyl 4-(4-chloro benzamido)piperidine-1-carboxylic acid ester (1o)

By using p-chlorobenzoic acid and tert-butyl 4-amino-piperidine-1-carboxylic acid ester as raw materials, the synthesis and post-treatment were carried out according to the same procedure as in Preparation Example 2. 3.3 g of white solid was obtained with the yield of 99%. m.p.: 156-158° C.; $^1$H NMR (500 MHz, CDCl$_3$): δ=7.69 (d, 2H, J=8.5 Hz, Ar—H), 7.39 (d, 2H, J=8.5 Hz, Ar—H), 6.06 (s, 1H, NH), 4.09 (m, 3H, CH+CH$_2$), 2.89 (t, 2H, J=12.5 Hz, CH$_2$), 2.00 (m, 2H, CH$_2$), 1.43 (m, 11H, CH$_2$+CH$_3$) ppm; ESI-MS: m/z=339 [M+H]$^+$.

Preparation Example 15. tert-butyl 4-(4-methoxy benzamido)piperidine-1-carboxylic acid ester (1p)

By using p-methoxybenzoic acid and tert-butyl 4-amino-piperidine-1-carboxylic acid ester as raw materials, the synthesis and post-treatment were carried out according to the same procedure as in Preparation Example 2. 3.3 g of white solid was obtained with the yield of 98%. m.p.: 144-146° C.; $^1$H NMR (500 MHz, CDCl$_3$): δ=7.71 (d, 2H, J=9.0 Hz, Ar—H), 6.89 (d, 2H, J=8.5 Hz, Ar—H), 6.05 (s, 1H, NH), 4.09 (m, 3H, CH+CH$_2$), 3.83 (s, 3H, CH$_3$), 2.88 (m, 2H, CH$_2$), 2.00 (m, 2H, CH$_2$), 1.45 (m, 11H, CH$_2$+CH$_3$) ppm; ESI-MS: m/z=335 [M+H]$^+$.

Preparation Example 16. tert-butyl 4-(morpholin-4-oyl)piperidine-1-carboxylic acid ester (1q)

By using morpholine as a raw material, the synthesis and post-treatment were carried out according to the same procedure as in Preparation Example 1. 2.8 g of white solid was obtained with the yield of 94%. m.p.: 122-124° C.; $^1$H NMR (500 MHz, CDCl$_3$): δ=4.14 (m, 2H, CH$_2$), 3.67 (m, 4H, CH$_2$), 3.61 (brs, 2H, CH$_2$), 3.51 (brs, 2H, CH$_2$), 2.75 (m, 2H, CH$_2$), 2.59 (m, 1H, CH), 1.67 (m, 4H, CH$_2$), 1.45 (s, 9H, CH$_3$) ppm; ESI-MS: m/z=299 [M+H]$^+$.

Preparation Example 17. tert-butyl 3-(pyrazin-2-yl carbamoyl)piperidine-1-carboxylic acid ester (1r)

By using 1-(tert-butyloxycarbonyl)piperidine-3-carboxylic acid as a raw material, the synthesis and post-treatment were carried out according to the same procedure as in Preparation Example 1. 2.1 g white viscous product was obtained with the yield of 67%. $^1$H NMR (500 MHz, CDCl$_3$): δ=9.53 (d, 1H, J=2.0 Hz, pyrazine-H), 8.52 (brs, 1H, NH), 8.34 (d, 1H, J=3.5 Hz, pyrazine-H), 8.25 (m, 1H, pyrazine-H), 4.09 (m, 1H, CH$_2$), 3.84 (m, 1H, CH$_2$), 3.25 (m, 1H, CH$_2$), 3.01 (m, 1H, CH$_2$), 2.54 (m, 1H, CH), 1.95 (m, 4H, CH$_2$), 1.47 (s, 9H, CH$_3$) ppm; ESI-MS: m/z=307 [M+H]$^+$.

Preparation Example 18. tert-butyl 3-(4-chlorophenyl carbamoyl)piperidine-1-carboxylic acid ester (1s)

By using 4-chloro aniline and 1-(tert-butyloxycarbonyl) piperidine-3-carboxylic acid as a raw material, the synthesis and post-treatment were carried out according to the same procedure as in Preparation Example 1. 1.9 g white viscous product was obtained with the yield of 55%. $^1$H NMR (500 MHz, CDCl$_3$): δ=8.42 (brs, 1H, NH), 7.54 (d, 2H, J=11.0 Hz, Ar—H), 7.26 (d, 2H, J=11.0 Hz, Ar—H), 3.76 (m, 1H, CH$_2$), 3.57 (m, 2H, CH$_2$), 3.29 (m, 1H, CH$_2$), 2.51 (m, 1H, CH), 2.11 (m, 1H, CH$_2$), 1.86 (m, 3H, CH$_2$), 1.47 (s, 9H, CH$_3$) ppm; ESI-MS: m/z=339 [M+H]$^+$.

Preparation Example 19. N-(pyrazin-2-yl)piperidine-4-formamide (2a, 2b)

Trifluoroacetic acid (15 mL) was added dropwise into a reactant 1a (3.06 g, 10 mmol) dissolved in 40 mL CH$_2$Cl$_2$. The reaction was carried out for 1 h at the room temperature. The reaction mixture was evaporated under a reduced pressure to give a product as colorless oil to be used directly in the next step.

Preparation Example 20. 1-(pyrazin-2-oyl)piperazine (2c)

By using tert-butyl 4-(pyrazin-2-oyl)piperazine-1-carboxyclic acid ester (1c) as a raw material, the synthesis and post-treatment were carried out according to the same procedure as in Preparation Example 19. The obtained product was used directly in the next step.

Preparation Example 21. N-(4-fluorophenyl)piperidine-4-formamide (2d)

By using tert-butyl 4-(fluorophenyl carbamoyl)piperidine-1-carboxyclic acid ester (1d) as a raw material, the synthesis and post-treatment were carried out according to the same procedure as in Preparation Example 19. The obtained product was used directly in the next step.

Preparation Example 22. N-(benzoyl phenyl)piperidine-4-formamide (2e)

By using tert-butyl 4-(4-benzoyl phenyl carbamoyl)piperidine-1-carboxyclic acid ester (1e) as a raw material, the synthesis and post-treatment were carried out according to the same procedure as in Preparation Example 19. The obtained product was used directly in the next step.

Preparation Example 23. N-(biphenyl)piperidine-4-formamide (2f)

By using tert-butyl 4-(biphenyl-4-yl carbamoyl)piperidine-1-carboxylic acid ester (1f) as a raw material, the synthesis and post-treatment were carried out according to the same procedure as in Preparation Example 19. The obtained product was used directly in the next step.

Preparation Example 24. N-(4-chlorophenyl)piperidine-4-formamide (2g)

By using tert-butyl 4-(chlorophenyl carbamoyl)piperidine-1-carboxyclic acid ester (1g) as a raw material, the synthesis and post-treatment were carried out according to the same procedure as in Preparation Example 19. The obtained product was used directly in the next step.

Preparation Example 25. N-(4-methoxy phenyl)piperidine-4-formamide (2h)

By using tert-butyl 4-(4-methoxy phenyl carbamoyl)piperidine-1-carboxyclic acid ester (1h) as a raw material, the synthesis and post-treatment were carried out according to the same procedure as in Preparation Example 19. The obtained product was used directly in the next step.

Preparation Example 26. N-(isoxazol-3-yl)piperidine-4-formamide (2i)

By using tert-butyl 4-(isoxazol-3-yl carbamoyl)piperidine-1-carboxyclic acid ester (1i) as a raw material, the synthesis and post-treatment were carried out according to the same procedure as in Preparation Example 19. The obtained product was used directly in the next step.

Preparation Example 27.
N-(thiazole-2-yl)piperidine-4-formamide (2j)

By using tert-butyl 4-(thiazol-2-yl carbamoyl)piperidine-1-carboxyclic acid ester (1j) as a raw material, the synthesis and post-treatment were carried out according to the same procedure as in Preparation Example 19. The obtained product was used directly in the next step.

Preparation Example 28.
N-(pyridin-2-yl)piperidine-4-formamide (2k)

By using tert-butyl 4-(pyridin-2-yl carbamoyl)piperidine-1-carboxyclic acid ester (1k) as a raw material, the synthesis and post-treatment were carried out according to the same procedure as in Preparation Example 19. The obtained product was used directly in the next step.

Preparation Example 29.
N-(pyridin-3-yl)piperidine-4-formamide (2l)

By using tert-butyl 4-(pyridin-3-yl carbamoyl)piperidine-1-carboxyclic acid ester (1l) as a raw material, the synthesis and post-treatment were carried out according to the same procedure as in Preparation Example 19. The obtained product was used directly in the next step.

Preparation Example 30.
N-(4-chlorophenyl)piperazine-4-formamide (2m)

By using tert-butyl 4-(4-chlorophenyl carbamoyl)piperazine-1-carboxyclic acid ester (1m) as a raw material, the synthesis and post-treatment were carried out according to the same procedure as in Preparation Example 19. The obtained product was used directly in the next step.

Preparation Example 31. N-(4-methoxy phenyl)piperazine-4-formamide (2n)

By using tert-butyl 4-(4-methoxy phenyl carbamoyl)piperazine-1-carboxyclic acid ester (1n) as a raw material, the synthesis and post-treatment were carried out according to the same procedure as in Preparation Example 19. The obtained product was used directly in the next step.

Preparation Example 32.
4-chloro-N-(piperidin-4-yl)benzamide (2o)

By using tert-butyl 4-(4-chloro benzamido)piperidine-1-carboxyclic acid ester (1o) as a raw material, the synthesis and post-treatment were carried out according to the same procedure as in Preparation Example 19. The obtained product was used directly in the next step.

Preparation Example 33.
4-methoxy-N-(piperidin-4-yl)benzamide (2p)

By using tert-butyl 4-(4-methoxy benzamido)piperidine-1-carboxyclic acid ester (1p) as a raw material, the synthesis and post-treatment were carried out according to the same procedure as in Preparation Example 19. The obtained product was used directly in the next step.

Preparation Example 34.
morpholinyl(piperidin-4-yl)ketone (2q)

By using tert-butyl 4-(morpholin-4-oyl)piperidine-1-carboxyclic acid ester (1q) as a raw material, the synthesis and post-treatment were carried out according to the same procedure as in Preparation Example 19. The obtained product was used directly in the next step.

Preparation Example 35.
N-(pyrazin-2-yl)piperidine-3-formamide (2r)

By using tert-butyl 3-(pyrazin-2-yl carbamoyl)piperidine-1-carboxyclic acid ester (1r) as a raw material, the synthesis and post-treatment were carried out according to the same procedure as in Preparation Example 19. The obtained product was used directly in the next step.

Preparation Example 36.
N-(4-chlorophenyl)piperidine-3-formamide (2s)

By using tert-butyl 3-(4-chlorophenyl carbamoyl)piperidine-1-carboxyclic acid ester (1s) as a raw material, the synthesis and post-treatment were carried out according to the same procedure as in Preparation Example 19. The obtained product was used directly in the next step.

Preparation Example 37. 4-(pyrazin-2-yl carbamoyl)piperidin-1-oyl-Phe-OMe (3a)

Methyl phenylalaninate hydrochloride (1.9 g, 9 mmol) dissolved in a mixed solution of 10 mL saturated $NaHCO_3$ solution and 10 mL $CH_2Cl_2$ was cooled to 0° C. in an ice-bath. Triphosgene (0.9 g, 3 mmol) was added to the mixture. The reaction was carried out for 15 min at the temperature of 0° C. Thereafter, the reaction mixture was stranded to separate an organic layer. The aqueous layer was extracted with $CH_2Cl_2$ (15 mL*3). The organic layers were combined, dried over anhydrous $Na_2SO_4$, and evaporated under a reduced pressure to remove the solvent. N-(pyrazin-2-yl)piperidine-4-formamide (2a, 1.2 g, 6 mmol) as a raw material dissolved in 15 mL $CH_2Cl_2$ was added dropwise to the above freshly prepared isocyanate. The reaction was carried out for 1 h at the room temperature. The reaction mixture was evaporated under a reduced pressure to remove the solvent. The resultant product was subjected to column chromatography to give 1.6 g of white solid with the yield of 65%. m.p.: 145-147° C.; $^1$H NMR (500 MHz, $CDCl_3$): δ=9.56 (s, 1H, pyrazine-H), 8.37 (d, 1H, J=2.5 Hz, pyrazine-H), 8.25 (s, 1H, pyrazine-H), 8.02 (s, 1H, NH), 7.30 (m, 3H, Ar—H), 7.11 (d, 2H, J=7.0 Hz, Ar—H), 4.93 (d, 1H, J=7.5 Hz, NH), 4.82 (q, 1H, J=6.5 Hz, CH), 4.04 (d, 1H, J=13.5 Hz, $CH_2$), 3.92 (d, 1H, J=13.5 Hz, $CH_2$), 3.74 (s, 3H, $CH_3$), 3.15 (m, 2H, $CH_2$), 2.88 (m, 2H, $CH_2$), 2.53 (m, 1H, CH), 1.94 (d, 2H, J=12.5 Hz, $CH_2$), 1.78 (m, 2H, $CH_2$) ppm; ESI-MS: m/z=412 [M+H]$^+$.

Preparation Example 38. 4-(pyrazin-2-yl carbamoyl)piperidin-1-oyl-Leu-OMe (3b)

By using methyl leucinate hydrochloride as a raw material, the synthesis and post-treatment were carried out according to the same procedure as in Preparation Example 37. 2.0 g white solid was obtained with the yield of 87%. m.p.: 75-77° C.; $^1$H NMR (500 MHz, $CDCl_3$): δ=9.55 (s, 1H, pyrazine-H), 8.36 (d, 1H, J=2.0 Hz, pyrazine-H), 8.25 (m, 2H, pyrazine-H+NH), 4.97 (d, 1H, J=7.5 Hz, NH), 4.53

(q, 1H, J=8.0 Hz, CH), 4.06 (m, 2H, CH$_2$), 3.74 (s, 3H, CH$_3$), 2.92 (q, 2H, J=13.0 Hz, CH$_2$), 2.57 (m, 1H, CH), 1.97 (m, 2H, CH$_2$), 1.80 (m, 2H, CH$_2$), 1.68 (m, 1H, CH$_2$), 1.63 (m, 1H, CH$_2$), 1.52 (m, 1H, CH), 0.95 (dd, 6H, J=6.5, 2.0 Hz, CH$_3$) ppm; ESI-MS: m/z=378 [M+H]$^+$.

Preparation Example 39. 4-(pyrazin-2-oyl)piperazin-1-oyl-Leu-OMe (3c)

By using methyl leucinate hydrochloride and 1-(pyrazin-2-oyl)piperazine (2c) as raw materials, the synthesis and post-treatment were carried out according to the same procedure as in Preparation Example 37. 2.0 g white solid was obtained with the yield of 92%. m.p.: 134-136° C.; $^1$H NMR (500 MHz, CDCl$_3$): δ=9.00 (s, 1H, pyrazine-H), 8.67 (d, 1H, J=1.5 Hz, pyrazine-H), 8.56 (s, 1H, pyrazine-H), 4.92 (d, 1H, J=7.0 Hz, NH), 4.52 (q, 1H, J=8.0 Hz, CH), 3.85 (m, 2H, CH$_2$), 3.75 (s, 3H, CH$_3$), 3.71 (m, 2H, CH$_2$), 3.53 (m, 4H, CH$_2$), 1.65 (m, 2H, CH+CH$_2$), 1.54 (m, 1H, CH$_2$), 0.95 (dd, 6H, J=6.0, 2.5 Hz, CH$_3$) ppm; ESI-MS: m/z=364 [M+H]$^+$.

Preparation Example 40. 4-(4-fluorophenyl carbamoyl)piperidin-1-oyl-Leu-OMe (3d)

By using N-(4-fluorophenyl)piperidine-4-formamide (2d) as a raw material, the synthesis and post-treatment were carried out according to the same procedure as in Preparation Example 37. 2.3 g white solid was obtained with the yield of 99%. m.p.: 63-65° C.; $^1$H NMR (500 MHz, CDCl$_3$): δ=7.48 (dd, 2H, J=8.5, 5.0 Hz, Ar—H), 7.28 (s, 1H, NH), 7.01 (t, 2H, J=8.5 Hz, Ar—H), 4.89 (d, 1H, J=8.0 Hz, NH), 4.52 (dd, 1H, J=14.0, 8.5 Hz, CH), 4.05 (t, 2H, J=14.0 Hz, CH$_2$), 3.74 (s, 3H, CH$_3$), 2.91 (q, 2H, J=10.5 Hz, CH$_2$), 2.43 (m, 1H, CH), 1.95 (d, 2H, J=13.0 Hz, CH$_2$), 1.79 (m, 2H, CH$_2$), 1.71 (m, 2H, CH$_2$+CH), 1.53 (m, 1H, CH$_2$), 0.96 (d, 6H, J=6.5 Hz, CH$_3$) ppm; ESI-MS: m/z=395 [M+H]$^+$.

Preparation Example 41. 4-(4-benzoyl phenyl carbamoyl)piperidin-1-oyl-Leu-OMe (3e)

By using N-(benzoyl phenyl)piperidine-4-formamide (2e) as a raw material, the synthesis and post-treatment were carried out according to the same procedure as in Preparation Example 37. 2.8 g white solid was obtained with the yield of 96%. m.p.: 71-73° C.; $^1$H NMR (500 MHz, CDCl$_3$): δ=7.82 (d, 2H, J=8.5 Hz, Ar—H), 7.77 (d, 2H, J=7.0 Hz, Ar—H), 7.67 (d, 2H, J=8.5 Hz, Ar—H), 7.58 (t, 1H, J=7.5 Hz, Ar—H), 7.55 (s, 1H, NH), 7.48 (t, 2H, J=7.5 Hz, Ar—H), 4.90 (d, 1H, J=8.0 Hz, NH), 4.53 (dd, 1H, J=13.5, 8.5 Hz, CH), 4.06 (t, 2H, J=13.5 Hz, CH$_2$), 3.74 (s, 3H, CH$_3$), 2.92 (q, 2H, J=11.0 Hz, CH$_2$), 2.47 (m, 1H, CH), 1.97 (d, 2H, J=13.0 Hz, CH$_2$), 1.84 (m, 2H, CH$_2$), 1.69 (m, 2H, CH$_2$), 1.52 (m, 1H, CH), 0.96 (d, 6H, J=6.5 Hz, CH$_3$) ppm; ESI-MS: m/z=480 [M+H]$^+$.

Preparation Example 42. 4-(biphenyl-4-yl carbamoyl)piperidin-1-oyl-Leu-OMe (3f)

By using N-(biphenyl)piperidine-4-formamide (2f) as a raw material, the synthesis and post-treatment were carried out according to the same procedure as in Preparation Example 37. 2.5 g white solid was obtained with the yield of 93%. m.p.: 67-69° C.; $^1$H NMR (500 MHz, CDCl$_3$): δ=7.59 (m, 6H, Ar—H), 7.43 (t, 2H, J=6.5 Hz, Ar—H), 7.33 (t, 1H, J=7.5 Hz, Ar—H), 7.27 (s, 1H, NH), 4.96 (d, 1H, J=5.5 Hz, NH), 4.53 (dd, 1H, J=13.5, 8.5 Hz, CH), 4.06 (m, 2H, CH$_2$), 3.75 (s, 3H, CH$_3$), 2.94 (q, 2H, J=11.5 Hz, CH$_2$), 2.47 (m, 1H, CH), 1.99 (d, 2H, J=11.0 Hz, CH$_2$), 1.82 (m, 2H, CH$_2$), 1.69 (m, 2H, CH$_2$), 1.53 (m, 1H, CH), 0.97 (d, 6H, J=6.5 Hz, CH$_3$) ppm; ESI-MS: m/z=452 [M+H]$^+$.

Preparation Example 43. 4-(4-chlorophenyl carbamoyl)piperidin-1-oyl-Leu-OMe (3g)

By using N-(4-chlorophenyl)piperidine-4-formamide (2g) as a raw material, the synthesis and post-treatment were carried out according to the same procedure as in Preparation Example 37. 2.4 g white solid was obtained with the yield of 98%. m.p.: 75-77° C.; $^1$H NMR (500 MHz, CDCl$_3$): δ=7.61 (s, 1H, NH), 7.50 (d, 2H, J=8.5 Hz, Ar—H), 7.27 (d, 2H, J=8.5 Hz, Ar—H), 5.06 (d, 1H, J=6.0 Hz, NH), 4.50 (dd, 1H, J=13.5, 8.5 Hz, CH), 4.04 (t, 2H, J=12.5 Hz, CH$_2$), 3.72 (s, 3H, CH$_3$), 2.88 (q, 2H, J=10.5 Hz, CH$_2$), 2.43 (m, 1H, CH), 1.93 (m, 2H, CH$_2$), 1.72 (m, 3H, CH$_2$+CH$_2$), 1.55 (m, 2H, CH+CH$_2$), 0.94 (d, 6H, J=6.5 Hz, CH$_3$) ppm; ESI-MS: m/z=410 [M+H]$^+$.

Preparation Example 44. 4-(4-methoxy phenyl carbamoyl)piperidin-1-oyl-Leu-OMe (3h)

By using N-(4-methoxy phenyl)piperidine-4-formamide (2h) as a raw material, the synthesis and post-treatment were carried out according to the same procedure as in Preparation Example 37. 1.8 g white solid was obtained with the yield of 73%. m.p.: 131-133° C.; $^1$H NMR (500 MHz, CDCl$_3$): δ=7.49 (s, 1H, NH), 7.42 (d, 2H, J=9.0 Hz, Ar—H), 6.84 (d, 2H, J=9.0 Hz, Ar—H), 5.01 (d, 1H, J=5.5 Hz, NH), 4.48 (dd, 1H, J=13.5, 8.5 Hz, CH), 4.03 (m, 2H, CH$_2$), 3.78 (s, 3H, CH$_3$), 3.72 (s, 3H, CH$_3$), 2.87 (q, 2H, J=12.0 Hz, CH$_2$), 2.41 (m, 1H, CH), 1.92 (d, 2H, J=13.0 Hz, CH$_2$), 1.80 (m, 2H, CH$_2$), 1.71 (m, 1H, CH$_2$), 1.59 (m, 1H, CH$_2$), 1.53 (m, 1H, CH), 0.94 (d, 6H, J=6.5 Hz, CH$_3$) ppm; ESI-MS: m/z=406 [M+H]$^+$.

Preparation Example 45. 4-(isoxazol-3-yl carbamoyl)piperidin-1-oyl-Leu-OMe (3i)

By using N-(isoxazol-3-yl)piperidine-4-formamide (2i) as a raw material, the synthesis and post-treatment were carried out according to the same procedure as in Preparation Example 37. 2.2 g white solid was obtained with the yield of 99%. m.p.: 137-139° C.; $^1$H NMR (500 MHz, CDCl$_3$): δ=9.88 (brs, 1H, NH), 8.32 (s, 1H, isoxazole-H), 7.14 (s, 1H, isoxazole-H), 4.97 (d, 1H, J=8.0 Hz, NH), 4.52 (dd, 1H, J=14.0, 8.5 Hz, CH), 4.06 (dd, 2H, J=30.0, 13.5 Hz, CH$_2$), 3.75 (s, 3H, CH$_3$), 2.95 (q, 2H, J=13.5 Hz, CH$_2$), 2.61 (m, 1H, CH), 1.97 (d, 2H, J=11.0 Hz, CH$_2$), 1.76 (m, 3H, CH$_2$+CH$_2$), 1.64 (m, 1H, CH$_2$), 1.54 (m, 1H, CH), 0.96 (d, 6H, J=7.0 Hz, CH$_3$) ppm; ESI-MS: m/z=367 [M+H]$^+$.

Preparation Example 46. 4-(thiazol-2-yl carbamoyl)piperidin-1-oyl-Leu-OMe (3j)

By using N-(thiazol-2-yl)piperidine-4-formamide (2j) as a raw material, the synthesis and post-treatment were carried out according to the same procedure as in Preparation Example 37. 2.2 g white solid was obtained with the yield of 97%. m.p.: 169-171° C.; $^1$H NMR (500 MHz, CDCl$_3$): δ=12.33 (s, 1H, NH), 7.38 (d, 1H, J=3.0 Hz, thiazole-H), 7.02 (d, 1H, J=3.5 Hz, thiazole-H), 5.17 (d, 1H, J=8.0 Hz, NH), 4.51 (dd, 1H, J=14.0, 8.5 Hz, CH), 4.03 (dd, 2H, J=35.0, 13.5 Hz, CH$_2$), 3.72 (s, 3H, CH$_3$), 2.91 (q, 2H, J=12.0 Hz, CH$_2$), 2.67 (m, 1H, CH), 1.87 (m, 4H, CH$_2$+

$CH_2$), 1.70 (m, 1H, $CH_2$), 1.56 (m, 2H, $CH+CH_2$), 0.93 (dd, 6H, J=6.0, 2.5 Hz, $CH_3$) ppm; ESI-MS: m/z=383 $[M+H]^+$.

Preparation Example 47. 4-(pyridin-2-yl carbamoyl) piperidin-1-oyl-Leu-OMe (3k)

By using N-(pyridin-2-yl)piperidine-4-formamide (2k) as a raw material, the synthesis and post-treatment were carried out according to the same procedure as in Preparation Example 37. 2.1 g white solid was obtained with the yield of 95%. m.p.: 69-71° C.; $^1H$ NMR (500 MHz, $CDCl_3$): δ=8.26 (m, 3H, NH+ pyridine-H), 7.72 (m, 1H, pyridine-H), 7.05 (m, 1H, pyridine-H), 4.91 (d, 1H, J=8.0 Hz, NH), 4.51 (m, 1H, CH), 4.02 (m, 2H, $CH_2$), 3.73 (s, 3H, $CH_3$), 2.91 (m, 2H, $CH_2$), 2.47 (m, 1H, CH), 1.95 (t, 2H, J=13.5 Hz, $CH_2$), 1.80 (m, 2H, $CH_2$), 1.71 (m, 1H, $CH_2$), 1.61 (m, 1H, $CH_2$), 1.52 (m, 1H, CH), 0.94 (dd, 6H, J=6.5, 2.5 Hz, $CH_3$) ppm; ESI-MS: m/z=377 $[M+H]^+$.

Preparation Example 48. 4-(pyridin-3-yl carbamoyl) piperidin-1-oyl-Leu-OMe (3l)

By using N-(pyridin-3-yl)piperidine-4-formamide (2l) as a raw material, the synthesis and post-treatment were carried out according to the same procedure as in Preparation Example 37. 2.0 g white solid was obtained with the yield of 92%. m.p.: 61-63° C.; $^1H$ NMR (500 MHz, $CDCl_3$): δ=8.66 (m, 2H, NH+ pyridine-H), 8.31 (d, 1H, J=4.5 Hz, pyridine-H), 8.22 (d, 1H, J=8.5 Hz, pyridine-H), 7.27 (dd, 1H, J=8.5, 4.5 Hz, pyridine-H), 5.20 (d, 1H, J=8.5 Hz, NH), 4.48 (m, 1H, CH), 4.04 (t, 2H, J=13.0 Hz, $CH_2$), 3.70 (s, 3H, $CH_3$), 2.86 (q, 2H, J=12.0 Hz, $CH_2$), 2.51 (m, 1H, CH), 1.91 (t, 2H, J=12.5 Hz, $CH_2$), 1.73 (m, 3H, $CH_2+CH_2$), 1.55 (m, 2H, $CH+CH_2$), 0.93 (d, 6H, J=6.5 Hz, $CH_3$) ppm; ESI-MS: m/z=377 $[M+H]^+$.

Preparation Example 49. 4-(4-chlorophenyl carbamoyl)piperazin-1-oyl-Leu-OMe (3m)

By using N-(4-chlorophenyl)piperazine-4-formamide (2m) as a raw material, the synthesis and post-treatment were carried out according to the same procedure as in Preparation Example 37. 1.8 g white solid was obtained with the yield of 73%. m.p.: 200-202° C.; $^1H$ NMR (500 MHz, $CDCl_3$): δ=7.31 (d, 2H, J=8.5 Hz, Ar—H), 7.23 (d, 2H, J=8.5 Hz, Ar—H), 6.66 (s, 1H, NH), 4.91 (d, 1H, J=7.5 Hz, NH), 4.49 (m, 1H, CH), 3.72 (s, 3H, $CH_3$), 3.51 (m, 8H, $CH_2$), 1.65 (m, 2H, $CH_2$), 1.52 (m, 1H, $CH_2$), 0.94 (d, 6H, J=6.5 Hz, $CH_3$) ppm; ESI-MS: m/z=411 $[M+H]^+$.

Preparation Example 50. 4-(4-methoxy phenyl carbamoyl)piperazine-1-oyl-Leu-OMe (3n)

By using N-(4-methoxy phenyl)piperazine-4-formamide (2n) as a raw material, the synthesis and post-treatment were carried out according to the same procedure as in Preparation Example 37. 2.4 g white solid was obtained with the yield of 99%. m.p.: 197-199° C.; $^1H$ NMR (500 MHz, $CDCl_3$): δ=7.24 (d, 2H, J=9.0 Hz, Ar—H), 6.84 (d, 2H, J=9.0 Hz, Ar—H), 6.32 (s, 1H, NH), 4.84 (d, 1H, J=7.5 Hz, NH), 4.52 (m, 1H, CH), 3.78 (s, 3H, $CH_3$), 3.74 (s, 3H, $CH_3$), 3.54 (m, 8H, $CH_2$), 1.65 (m, 2H, $CH_2$), 1.53 (m, 1H, $CH_2$), 0.95 (dd, 6H, J=6.5, 1.5 Hz, $CH_3$) ppm; ESI-MS: m/z=407 $[M+H]^+$.

Preparation Example 51. 4-(4-chloro benzamido)piperidin-1-oyl-Leu-OMe (3o)

By using 4-chloro-N-(piperidin-4-yl)benzamide (2o) as a raw material, the synthesis and post-treatment were carried out according to the same procedure as in Preparation Example 37. 2.1 g white solid was obtained with the yield of 84%. m.p.: 190-192° C.; $^1H$ NMR (500 MHz, $CDCl_3$): δ=7.72 (d, 2H, J=8.0 Hz, Ar—H), 7.40 (d, 2H, J=8.0 Hz, Ar—H), 6.25 (brs, 1H, NH), 4.98 (brs, 1H, NH), 4.46 (m, 1H, CH), 4.15 (m, 1H, CH), 3.97 (m, 2H, $CH_2$), 3.70 (s, 3H, $CH_3$), 2.97 (m, 2H, $CH_2$), 2.04 (m, 2H, $CH_2$), 1.67 (m, 2H, $CH_2$), 1.49 (m, 3H, $CH+CH_2$), 0.93 (m, 6H, $CH_3$) ppm; ESI-MS: m/z=410 $[M+H]^+$.

Preparation Example 52. 4-(4-methoxy benzamido)piperidin-1-oyl-Leu-OMe (3p)

By using 4-methoxy-N-(piperidin-4-yl)benzamide (2p) as a raw material, the synthesis and post-treatment were carried out according to the same procedure as in Preparation Example 37. 2.4 g white solid was obtained with the yield of 98%. m.p.: 169-171° C.; $^1H$ NMR (500 MHz, $CDCl_3$): δ=7.72 (d, 2H, J=8.5 Hz, Ar—H), 6.92 (d, 2H, J=8.5 Hz, Ar—H), 6.05 (brs, 1H, NH), 4.87 (d, 1H, J=8.0 Hz, NH), 4.48 (m, 1H, CH), 4.14 (m, 1H, CH), 3.97 (m, 2H, $CH_2$), 3.84 (s, 3H, $CH_3$), 3.71 (s, 3H, $CH_3$), 2.98 (m, 2H, $CH_2$), 2.04 (m, 2H, $CH_2$), 1.62 (m, 2H, $CH_2$), 1.49 (m, 3H, $CH+CH_2$), 0.94 (d, 6H, J=6.5 Hz, $CH_3$) ppm; ESI-MS: m/z=406 $[M+H]^+$.

Preparation Example 53. 4-(morpholin-4-oyl)piperidin-1-oyl-Leu-OMe (3q)

By using morpholinyl(piperidin-4-yl)ketone (2q) as a raw material, the synthesis and post-treatment were carried out according to the same procedure as in Preparation Example 37. 1.6 g of colorless oily product was obtained with the yield of 72%. $^1H$ NMR (500 MHz, $CDCl_3$): δ=4.87 (d, 1H, J=8.0 Hz, NH), 4.55 (m, 1H, CH), 4.00 (m, 2H, $CH_2$), 3.67 (m, 4H, $CH_2$), 3.62 (m, 2H, $CH_2$), 3.55 (s, 3H, $CH_3$), 3.50 (m, 2H, $CH_2$), 2.88 (m, 2H, $CH_2$), 2.62 (m, 1H, CH), 1.75 (m, 4H, $CH_2$), 1.62 (m, 2H, $CH_2$), 1.52 (m, 1H, CH), 0.91 (dd, 6H, J=6.5, 2.5 Hz, $CH_3$) ppm; ESI-MS: m/z=446 $[M+H]^+$.

Preparation Example 54. 3-(pyrazin-2-yl carbamoyl)piperidin-1-oyl-Leu-OMe (3r)

By using N-(pyrazin-2-yl)piperidine-3-formamide (2r) as a raw material, the synthesis and post-treatment were carried out according to the same procedure as in Preparation Example 37. 2.2 g of colorless oily product was obtained with the yield of 96%. $^1H$ NMR (500 MHz, $CDCl_3$): δ=9.51 (d, 1H, J=4.0 Hz, pyrazine-H), 9.44 and 9.00 (s, 1H, 50/50, NH), 8.32 (m, 1H, pyrazine-H), 8.27 (m, 1H, pyrazine-H), 5.73 and 5.11 (m, 1H, 50/50, NH), 4.58 (m, 1H, CH), 4.10 (m, 1H, $CH_2$), 4.05 and 3.58 (m, 1H, 50/50, $CH_2$), 3.71 and 3.55 (s, 3H, 50/50, $CH_3$), 3.38 and 2.92 (m, 1H, 50/50, $CH_2$), 3.18 (m, 1H, $CH_2$), 2.61 and 2.54 (m, 1H, 50/50, CH), 2.01 (m, 4H, $CH_2$), 1.60 (m, 2H, $CH_2$), 1.56 (m, 1H, CH), 0.92 (m, 6H, $CH_3$) ppm; ESI-MS: m/z=378 $[M+H]^+$.

Preparation Example 55. 3-(4-chlorophenyl carbamoyl)piperidin-1-oyl-Leu-OMe (3s)

By using N-(4-chlorophenyl)piperidine-3-formamide (2s) as a raw material, the synthesis and post-treatment were carried out according to the same procedure as in Preparation Example 37. 2.0 g of white solid was obtained with the yield of 82%. m.p.: 145-147° C.; $^1H$ NMR (500 MHz, $CDCl_3$): δ=9.15 and 9.01 (s, 1H, 50/50, NH), 7.72 and 7.59

(d, 2H, 50/50, J=11.0 Hz, Ar—H), 7.25 (m, 2H, Ar—H), 6.24 and 5.05 (brs, 1H, 50/50, NH), 4.49 (m, 1H, CH), 4.17 and 3.56 (m, 1H, 50/50, CH$_2$), 3.96 (m, 1H, CH$_2$), 3.73 and 3.34 (s, 3H, 50/50, CH$_3$), 3.38 and 3.25 (m, 1H, 50/50, CH$_2$), 2.89 and 2.59 (m, 1H, 50/50, CH$_2$), 2.27 (m, 1H, CH), 1.87 (m, 4H, CH$_2$), 1.61 (m, 2H, CH$_2$), 1.51 (m, 1H, CH), 0.91 (m, 6H, CH$_3$) ppm; ESI-MS: m/z=410 [M+H]$^+$.

Preparation Example 56. 4-(pyrazin-2-yl carbamoyl)piperidin-1-oyl-Phe (4a)

4-(pyrazin-2-yl carbamoyl)piperidin-1-oyl-Phe-OMe (0.41 g, 1 mmol) as a raw material was dissolved in 4 mL acetone. 4 mL of 0.5 N aqueous LiOH solution was added dropwise to the above solution. The reaction was carried out at the room temperature for 0.5 h. The resultant mixture was evaporated at a reduced pressure to remove acetone. The aqueous layer was adjusted to pH 3-4 with 1N HCl, and extracted with ethyl acetate (10 mL*3). The organic layers were combined, dried over anhydrous Na$_2$SO$_4$, and then evaporated at a reduced pressure to remove the solvent. The obtained product was used directly in the next step.

Preparation Example 57. 4-(pyrazin-2-yl carbamoyl)piperidin-1-oyl-Leu (4b)

By using 4-(pyrazin-2-yl carbamoyl)piperidin-1-oyl-Leu-OMe (3b) as a raw material, the synthesis and post-treatment were carried out according to the same procedure as in Preparation Example 57. The obtained product was used directly in the next step.

Preparation Example 58. 4-(pyrazin-2-oyl)piperazin-1-oyl-Leu (4c)

By using 4-(pyrazin-2-oyl)piperazin-1-oyl-Leu-OMe (3c) as a raw material, the synthesis and post-treatment were carried out according to the same procedure as in Preparation Example 56. The obtained product was used directly in the next step.

Preparation Example 59. 4-(4-fluorophenyl carbamoyl)piperidin-1-oyl-Leu (4d)

By using 4-(4-fluorophenyl carbamoyl)piperidin-1-oyl-Leu-OMe (3d) as a raw material, the synthesis and post-treatment were carried out according to the same procedure as in Preparation Example 56. The obtained product was used directly in the next step.

Preparation Example 60. 4-(4-benzoyl phenyl carbamoyl)piperidin-1-oyl-Leu (4e)

By using 4-(4-benzoyl phenyl carbamoyl)piperidin-1-oyl-Leu-OMe (3e) as a raw material, the synthesis and post-treatment were carried out according to the same procedure as in Preparation Example 56. The obtained product was used directly in the next step.

Preparation Example 61. 4-(biphenyl-4-yl carbamoyl)piperidin-1-oyl-Leu (4d)

By using 4-(biphenyl-4-yl carbamoyl)piperidin-1-oyl-Leu-OMe (3f) as a raw material, the synthesis and post-treatment were carried out according to the same procedure as in Preparation Example 56. The obtained product was used directly in the next step.

Preparation Example 62. 4-(4-chlorophenyl carbamoyl)piperidin-1-oyl-Leu (4g)

By using 4-(4-chlorophenyl carbamoyl)piperidin-1-oyl-Leu-OMe (3g) as a raw material, the synthesis and post-treatment were carried out according to the same procedure as in Preparation Example 56. The obtained product was used directly in the next step.

Preparation Example 63. 4-(4-methoxy phenyl carbamoyl)piperidin-1-oyl-Leu (4h)

By using 4-(4-methoxy phenyl carbamoyl)piperidin-1-oyl-Leu-OMe (3h) as a raw material, the synthesis and post-treatment were carried out according to the same procedure as in Preparation Example 56. The obtained product was used directly in the next step.

Preparation Example 64. 4-(isoxazol-3-yl carbamoyl)piperidin-1-oyl-Leu (4i)

By using 4-(isoxazol-3-yl carbamoyl)piperidin-1-oyl-Leu-OMe (3i) as a raw material, the synthesis and post-treatment were carried out according to the same procedure as in Preparation Example 56. The obtained product was used directly in the next step.

Preparation Example 65. 4-(thiazol-2-yl carbamoyl)piperidin-1-oyl-Leu (4j)

By using 4-(thiazol-2-yl carbamoyl)piperidin-1-oyl-Leu-OMe (3j) as a raw material, the synthesis and post-treatment were carried out according to the same procedure as in Preparation Example 56. The obtained product was used directly in the next step.

Preparation Example 66. 4-(pyridin-2-yl carbamoyl)piperidin-1-oyl-Leu (4k)

By using 4-(pyridin-2-yl carbamoyl)piperidin-1-oyl-Leu-OMe (3k) as a raw material, the synthesis and post-treatment were carried out according to the same procedure as in Preparation Example 56. The obtained product was used directly in the next step.

Preparation Example 67. 4-(pyridin-3-yl carbamoyl)piperidin-1-oyl-Leu (4l)

By using 4-(pyridin-3-yl carbamoyl)piperidin-1-oyl-Leu-OMe (3l) as a raw material, the synthesis and post-treatment were carried out according to the same procedure as in Preparation Example 56. The obtained product was used directly in the next step.

Preparation Example 68. 4-(4-chlorophenyl carbamoyl)piperazin-1-oyl-Leu (4m)

By using 4-(4-chlorophenyl carbamoyl)piperazin-1-oyl-Leu-OMe (3m) as a raw material, the synthesis and post-treatment were carried out according to the same procedure as in Preparation Example 56. The obtained product was used directly in the next step.

Preparation Example 69. 4-(4-methoxy phenyl carbamoyl)piperazin-1-oyl-Leu (4n)

By using 4-(4-methoxy phenyl carbamoyl)piperazin-1-oyl-Leu-OMe (3n) as a raw material, the synthesis and post-treatment were carried out according to the same procedure as in Preparation Example 56. The obtained product was used directly in the next step.

Preparation Example 70. 4-(4-chloro benzamido)piperidin-1-oyl-Leu (4o)

By using 4-(4-chloro benzamido)piperidin-1-oyl-Leu-OMe (3o) as a raw material, the synthesis and post-treatment were carried out according to the same procedure as in Preparation Example 56. The obtained product was used directly in the next step.

Preparation Example 71. 4-(4-methoxy benzamido)piperidin-1-oyl-Leu (4p)

By using 4-(4-methoxy benzamido)piperidin-1-oyl-Leu-OMe (3p) as a raw material, the synthesis and post-treatment were carried out according to the same procedure as in Preparation Example 56. The obtained product was used directly in the next step.

Preparation Example 72. 4-(morpholin-4-oyl)piperidin-1-oyl-Leu (4q)

By using 4-(morpholin-4-oyl)piperidin-1-oyl-Leu-OMe (3q) as a raw material, the synthesis and post-treatment were carried out according to the same procedure as in Preparation Example 56. The obtained product was used directly in the next step.

Preparation Example 73. 3-(pyrazin-2-yl carbamoyl)piperidin-1-oyl-Leu (4r)

By using 3-(pyrazin-2-yl carbamoyl)piperidin-1-oyl-Leu-OMe (3r) as a raw material, the synthesis and post-treatment were carried out according to the same procedure as in Preparation Example 56. The obtained product was used directly in the next step.

Preparation Example 74. 3-(4-chlorophenyl carbamoyl)piperidin-1-oyl-Leu (4s)

By using 3-(4-chlorophenyl carbamoyl)piperidin-1-oyl-Leu-OMe (3s) as a raw material, the synthesis and post-treatment were carried out according to the same procedure as in Preparation Example 56. The obtained product was used directly in the next step.

Preparation Example 75. Boc-Phe-Leu-epoxy ketone (7a)

By using Boc-L-Phe and Leu-epoxy ketone (6a) as raw materials, the synthesis and post-treatment were carried out according to the same procedure as in Preparation Example 2. 1.5 g white solid was obtained with a yield of 90%. m.p.: 151-153° C.; $^1$H NMR (500 MHz, CDCl$_3$): δ=7.20 (m, 5H, Ar—H), 6.18 (d, 1H, J=6.5 Hz, NH), 4.95 (d, 1H, J=6.5 Hz, NH), 4.57 (m, 1H, CH), 4.32 (m, 1H, CH), 3.24 (d, 1H, J=4.5 Hz, OCH$_2$), 3.03 (m, 2H, CH$_2$), 2.88 (d, 1H, J=4.5 Hz, OCH$_2$), 1.63 (m, 1H, CH), 1.49 (s, 3H, CH$_3$), 1.46 (m, 1H, CH$_2$), 1.43 (s, 9H, CH$_3$), 1.17 (m, 1H, CH$_2$), 0.92 (d, 3H, J=6.5 Hz, CH$_3$), 0.87 (d, 3H, J=6.5 Hz, CH$_3$) ppm; ESI-MS: m/z=419 [M+H]$^+$.

Preparation Example 76. Boc-Leu-Leu-epoxy ketone (7b)

By using Boc-L-Leu and Leu-epoxy ketone (6b) as raw materials, the synthesis and post-treatment were carried out according to the same procedure as in Preparation Example 2. 1.2 g white solid was obtained with a yield of 76%. m.p.: 184-186° C.; $^1$H NMR (500 MHz, CDCl$_3$): δ=6.46 (d, 1H, J=6.5 Hz, NH), 4.87 (d, 1H, J=8.5 Hz, NH), 4.59 (m, 1H, CH), 4.10 (m, 1H, CH), 3.31 (d, 1H, J=4.5 Hz, OCH$_2$), 2.90 (d, 1H, J=4.5 Hz, OCH$_2$), 1.63 (m, 4H, CH+CH$_2$), 1.52 (s, 3H, CH$_3$), 1.46 (m, 1H, CH$_2$), 1.43 (s, 9H, CH$_3$), 1.29 (m, 1H, CH$_2$), 0.93 (m, 12H, CH$_3$) ppm; ESI-MS: m/z=385 [M+H]$^+$.

Preparation Example 77. Phe-Leu-epoxy ketone (8a)

By using Boc-Phe-Leu-epoxy ketone (7a) as a raw material, the synthesis and post-treatment were carried out according to the same procedure as in Preparation Example 19. The obtained product was used directly in the next step.

Preparation Example 78. Leu-Leu-epoxy ketone (8b)

By using Boc-Leu-Leu-epoxy ketone (7b) as a raw material, the synthesis and post-treatment were carried out according to the same procedure as in Preparation Example 19. The obtained product was used directly in the next step.

Preparation Example 79. 4-(pyrazin-2-yl carbamoyl)piperidin-1-oyl-Phe-Leu-Leu-epoxy ketone (5a)

4-(pyrazin-2-yl carbamoyl)piperidin-1-oyl-Phe (4a, 0.5 g, 1.2 mmol) as a raw material was dissolved in 4 mL CH$_2$Cl$_2$. 1-hydroxy benzotriazole (0.16 g, 1.2 mmol) and N-(3-dimethylamino propyl)-N'-ethyl carbodiimide hydrochloride (0.35 g, 1.8 mmol) were added to the above obtained solution. After the reaction was carried out at the room temperature for 0.5 h, Leu-Leu-epoxy ketone (8b, 1 mmol) was added. The reaction was carried out at the room temperature for 3 h. 10 mL saturated NaHCO$_3$ was added to the resultant mixture. The organic layer was separated and washed with saturated saline (10 mL*1), dried over anhydrous Na$_2$SO$_4$, and then evaporated to remove the solvent. The residue was subjected to column chromatography to give 0.59 g white solid with a yield of 89%. $^1$H NMR (500 MHz, CDCl$_3$): δ=9.53 (s, 1H, pyrazine-H), 8.36 (d, 1H, J=2.0 Hz, pyrazine-H), 8.24 (s, 1H, pyrazine-H), 7.94 (s, 1H, NH), 7.25 (m, 5H, Ar—H), 6.60 (d, 1H, J=8.5 Hz, NH), 6.53 (d, 1H, J=7.0 Hz, NH), 4.95 (d, 1H, J=5.0 Hz, NH), 4.54 (m, 2H, CH+CH), 4.37 (m, 1H, CH), 3.88 (m, 2H, CH$_2$), 3.31 (d, 1H, J=5.0 Hz, OCH$_2$), 3.10 (m, 2H, CH$_2$), 2.87 (m, 3H, CH$_2$+OCH$_2$), 2.50 (m, 1H, CH), 1.89 (m, 2H, CH$_2$), 1.78 (m, 2H, CH$_2$), 1.61 (m, 2H, CH$_2$), 1.46 (m, 6H, CH+CH$_3$+CH$_2$), 1.30 (m, 1H, CH), 0.91 (m, 12H, CH$_3$) ppm; ESI-MS: m/z=664 [M+H]$^+$.

Preparation Example 80. 4-(pyrazin-2-yl carbamoyl)piperidin-1-oyl-Leu-Phe-Leu-epoxy ketone (5b)

By using 4-(pyrazin-2-yl carbamoyl)piperidin-1-oyl-Leu (4b) and Phe-Leu-epoxy ketone (8a) as raw materials, the synthesis and post-treatment were carried out according to the same procedure as in Preparation Example 81. 0.58 g white solid was obtained with a yield of 87%. $^1$H NMR (500 MHz, CDCl$_3$): δ=9.56 (s, 1H, pyrazine-H), 8.37 (d, 1H, J=2.5 Hz, pyrazine-H), 8.25 (s, 1H, pyrazine-H), 8.17 (s, 1H, NH), 7.20 (m, 5H, Ar—H), 6.83 (s, 1H, NH), 6.60 (d, 1H, J=8.0 Hz, NH), 4.82 (s, 1H, NH), 4.61 (q, 1H, J=7.0 Hz, CH), 4.55 (m, 1H, CH), 4.23 (m, 1H, CH), 3.95 (m, 2H, CH$_2$), 3.26 (d, 1H, J=4.5 Hz, OCH$_2$), 3.06 (m, 2H, CH$_2$), 2.87 (m, 3H, CH$_2$+OCH$_2$), 2.55 (m, 1H, CH), 1.96 (m, 2H, CH$_2$), 1.75 (m, 2H, CH$_2$), 1.61 (m, 2H, CH$_2$), 1.46 (m, 6H, CH+CH$_3$+CH$_2$), 1.21 (m, 1H, CH), 0.89 (m, 12H, CH$_3$) ppm; ESI-MS: m/z=664 [M+H]$^+$.

Preparation Example 81. 4-(pyrazin-2-oyl)piperazin-1-oyl-Leu-Phe-Leu-epoxy ketone (5c)

By using 4-(pyrazin-2-oyl)piperazin-1-oyl-Leu (4c) and Phe-Leu-epoxy ketone (8a) as raw materials, the synthesis and post-treatment were carried out according to the same procedure as in Preparation Example 81. 0.53 g white solid was obtained with a yield of 82%. $^1$H NMR (500 MHz, CDCl$_3$): δ=9.00 (s, 1H, pyrazine-H), 8.67 (d, 1H, J=2.5 Hz, pyrazine-H), 8.55 (s, 1H, pyrazine-H), 7.22 (m, 5H, Ar—H), 6.78 (d, 1H, J=8.0 Hz, NH), 6.50 (d, 1H, J=7.5 Hz, NH), 4.92 (s, 1H, NH), 4.63 (q, 1H, J=6.5 Hz, CH), 4.54 (m, 1H, CH), 4.28 (m, 1H, CH), 3.81 (m, 2H, CH$_2$), 3.67 (m, 2H, CH$_2$), 3.43 (m, 4H, CH$_2$), 3.23 (d, 1H, J=5.0 Hz, OCH$_2$), 3.05 (m, 2H, CH$_2$), 2.87 (d, 1H, J=5.0 Hz, OCH$_2$), 1.60 (m, 2H, CH$_2$), 1.48 (m, 7H, CH$_3$+CH$_2$), 0.89 (m, 12H, CH$_3$) ppm; ESI-MS: m/z=650 [M+H]$^+$.

Preparation Example 82. 4-(4-fluorophenyl carbamoyl)piperidin-1-oyl-Leu-Phe-Leu-epoxy ketone (5d)

By using 4-(4-fluorophenyl carbamoyl)piperidin-1-oyl-Leu (4d) as a raw material, the synthesis and post-treatment were carried out according to the same procedure as in Preparation Example 81. 0.47 g white solid was obtained with a yield of 69%. $^1$H NMR (500 MHz, CDCl$_3$): δ=7.49 (m, 3H, Ar-H+NH), 7.20 (m, 5H, Ar—H), 7.01 (t, 2H, J=8.5 Hz, Ar—H), 6.87 (brs, 1H, NH), 6.62 (d, 1H, J=6.0 Hz, NH), 4.88 (brs, 1H, NH), 4.61 (q, 1H, J=6.5 Hz, CH), 4.52 (m, 1H, CH), 4.23 (m, 1H, CH), 3.94 (t, 2H, J=14.5 Hz, CH$_2$), 3.21 (d, 1H, J=4.5 Hz, OCH$_2$), 3.05 (m, 2H, CH$_2$), 2.83 (m, 3H, CH$_2$+OCH$_2$), 2.44 (m, 1H, CH), 1.92 (d, 2H, J=11.5 Hz, CH$_2$), 1.76 (m, 2H, CH$_2$), 1.47 (m, 7H, CH$_3$+CH$_2$), 1.25 (m, 2H, CH+CH), 0.89 (m, 12H, CH$_3$) ppm; ESI-MS: m/z=680 [M+H]$^+$.

Preparation Example 83. 4-(4-benzoyl phenyl carbamoyl)piperidin-1-oyl-Leu-Phe-Leu-epoxy ketone (5e)

By using 4-(4-benzoyl phenyl carbamoyl)piperidin-1-oyl-Leu (4e) as a raw material, the synthesis and post-treatment were carried out according to the same procedure as in Preparation Example 81. 0.49 g white solid was obtained with a yield of 64%. $^1$H NMR (500 MHz, CDCl$_3$): δ=7.93 (s, 1H, NH), 7.81 (d, 2H, J=9.0 Hz, Ar—H), 7.76 (d, 2H, J=7.5 Hz, Ar—H), 7.68 (d, 2H, J=8.5 Hz, Ar—H), 7.59 (t, 1H, J=7.5 Hz, Ar—H), 7.48 (t, 2H, J=8.0 Hz, Ar—H), 7.24 (m, 5H, Ar—H), 6.80 (d, 1H, J=7.5 Hz, NH), 6.61 (d, 1H, J=7.5 Hz, NH), 4.88 (d, 1H, J=6.0 Hz, NH), 4.62 (q, 1H, J=7.0 Hz, CH), 4.54 (m, 1H, CH), 4.23 (m, 1H, CH), 3.95 (t, 2H, J=14.5 Hz, CH$_2$), 3.23 (d, 1H, J=5.0 Hz, OCH$_2$), 3.09 (m, 2H, CH$_2$), 2.84 (m, 3H, CH$_2$+OCH$_2$), 2.49 (m, 1H, CH), 1.92 (d, 2H, J=13.0 Hz, CH$_2$), 1.78 (m, 2H, CH$_2$), 1.62 (m, 2H, CH$_2$), 1.47 (m, 5H, CH$_3$+CH$_2$), 1.25 (m, 2H, CH+CH), 0.89 (m, 12H, CH$_3$) ppm; ESI-MS: m/z=766 [M+H]$^+$.

Preparation Example 84. 4-(biphenyl-4-yl carbamoyl)piperidin-1-oyl-Leu-Phe-Leu-epoxy ketone (5f)

By using 4-(biphenyl-4-yl carbamoyl)piperidin-1-oyl-Leu (4f) as a raw material, the synthesis and post-treatment were carried out according to the same procedure as in Preparation Example 81. 0.49 g white solid was obtained with a yield of 67%. $^1$H NMR (500 MHz, CDCl$_3$): δ=7.58 (m, 6H, Ar—H), 7.43 (m, 3H, Ar-H+NH), 7.34 (t, 1H, J=7.5 Hz, Ar—H), 7.22 (m, 5H, Ar—H), 6.77 (d, 1H, J=6.5 Hz, NH), 6.58 (d, 1H, J=8.5 Hz, NH), 4.77 (d, 1H, J=6.0 Hz, NH), 4.62 (q, 1H, J=7.0 Hz, CH), 4.56 (m, 1H, CH), 4.23 (m, 1H, CH), 3.95 (m, 2H, CH$_2$), 3.24 (d, 1H, J=5.0 Hz, OCH$_2$), 3.08 (m, 2H, CH$_2$), 2.85 (m, 3H, CH$_2$+OCH$_2$), 2.46 (m, 1H, CH), 1.95 (d, 2H, J=11.5 Hz, CH$_2$), 1.70 (m, 4H, CH$_2$+CH$_2$), 1.48 (m, 5H, CH$_3$+CH$_2$), 1.23 (m, 2H, CH+CH), 0.90 (m, 12H, CH$_3$) ppm; ESI-MS: m/z=738 [M+H]$^+$.

Preparation Example 85. 4-(4-chlorophenyl carbamoyl)piperidin-1-oyl-Leu-Phe-Leu-epoxy ketone (5g)

By using 4-(4-chlorophenyl carbamoyl)piperidin-1-oyl-Leu (4g) as a raw material, the synthesis and post-treatment were carried out according to the same procedure as in Preparation Example 81. 0.58 g white solid was obtained with a yield of 84%. $^1$H NMR (500 MHz, CDCl$_3$): δ=7.63 (s, 1H, NH), 7.48 (d, 2H, J=8.5 Hz, Ar—H), 7.25 (m, 5H, Ar—H), 7.16 (d, 2H, J=6.5 Hz, Ar—H), 6.83 (d, 1H, J=8.0 Hz, NH), 6.62 (d, 1H, J=8.0 Hz, NH), 4.88 (d, 1H, J=6.0 Hz, NH), 4.61 (q, 1H, J=7.0 Hz, CH), 4.53 (m, 1H, CH), 4.21 (m, 1H, CH), 3.93 (t, 2H, J=13.5 Hz, CH$_2$), 3.21 (d, 1H, J=5.0 Hz, OCH$_2$), 3.04 (m, 2H, CH$_2$), 2.82 (m, 3H, CH$_2$+OCH$_2$), 2.42 (m, 1H, CH), 1.90 (d, 2H, J=12.5 Hz, CH$_2$), 1.76 (m, 2H, CH$_2$), 1.60 (m, 2H, CH+CH), 1.46 (m, 7H, CH$_3$+CH$_2$), 0.88 (m, 12H, CH$_3$) ppm; ESI-MS: m/z=696 [M+H]$^+$.

Preparation Example 86. 4-(4-methoxy phenyl carbamoyl)piperidin-1-oyl-Leu-Phe-Leu-epoxy ketone (5h)

By using 4-(4-methoxy phenyl carbamoyl)piperidin-1-oyl-Leu (4h) as a raw material, the synthesis and post-treatment were carried out according to the same procedure as in Preparation Example 81. 0.46 g white solid was obtained with a yield of 67%. $^1$H NMR (500 MHz, CDCl$_3$): δ=7.42 (m, 3H, Ar-H+NH), 7.24 (m, 5H, Ar—H), 6.85 (m, 3H, Ar-H+NH), 6.65 (d, 1H, J=6.5 Hz, NH), 4.86 (brs, 1H, NH), 4.56 (m, 2H, CH+CH), 4.22 (m, 1H, CH), 3.94 (m, 2H, CH$_2$), 3.78 (s, 3H, CH$_3$), 3.22 (d, 1H, J=4.5 Hz, OCH$_2$), 3.10 (m, 2H, CH$_2$), 2.83 (m, 3H, CH$_2$+OCH$_2$), 2.42 (m, 1H, CH), 1.85 (m, 4H, CH$_2$+CH$_2$), 1.61 (m, 2H, CH$_2$), 1.47 (m, 5H, CH$_3$+CH$_2$), 1.25 (m, 2H, CH+CH), 0.87 (m, 12H, CH$_3$) ppm; ESI-MS: m/z=692 [M+H]$^+$.

Preparation Example 87. 4-(isoxazol-3-yl carbamoyl)piperidin-1-oyl-Leu-Phe-Leu-epoxy ketone (5i)

By using 4-(isoxazol-3-yl carbamoyl)piperidin-1-oyl-Leu (4i) as a raw material, the synthesis and post-treatment were carried out according to the same procedure as in Preparation Example 81. 0.42 g white solid was obtained with a yield of 64%. $^1$H NMR (500 MHz, d6-DMSO): δ=9.38 (s, 1H, NH), 8.30 (d, 1H, J=1.0 Hz, isoxazole-H), 7.22 (m, 5H, Ar—H), 7.12 (d, 1H, J=1.0 Hz, isoxazole-H), 6.91 (brs, 1H, NH), 6.61 (d, 1H, J=8.0 Hz, NH), 4.90 (brs, 1H, NH), 4.59 (m, 2H, CH+CH), 4.27 (m, 1H, CH), 3.95 (m, 2H, CH$_2$), 3.27 (d, 1H, J=4.5 Hz, OCH$_2$), 3.07 (m, 2H, CH$_2$), 2.87 (m, 3H, CH$_2$+OCH$_2$), 2.56 (m, 1H, CH), 1.94 (m, 2H, CH$_2$), 1.69 (m, 4H, CH$_2$+CH$_2$), 1.48 (m, 5H, CH$_3$+CH$_2$), 1.25 (m, 2H, CH+CH), 0.89 (m, 12H, CH$_3$) ppm; ESI-MS: m/z=653 [M+H]$^+$.

Preparation Example 88. 4-(thiazol-2-yl carbamoyl) piperidin-1-oyl-Leu-Phe-Leu-epoxy ketone (5j)

By using 4-(thiazol-2-yl carbamoyl)piperidin-1-oyl-Leu (4j) as a raw material, the synthesis and post-treatment were carried out according to the same procedure as in Preparation Example 81. 0.49 g white solid was obtained with a yield of 74%. $^1$H NMR (500 MHz, CDCl$_3$): δ=11.47 (brs, 1H, NH), 7.54 (m, 2H, thiazole-H+NH), 7.18 (m, 6H, Ar-H+NH), 7.03 (d, 1H, J=3.5 Hz, thiazole-H), 5.08 (brs, 1H, NH), 4.72 (q, 1H, J=7.0 Hz, CH), 4.61 (m, 1H, CH), 4.42 (m, 1H, CH), 3.94 (dd, 2H, J=26.0, 13.5 Hz, CH$_2$), 3.28 (d, 1H, J=5.0 Hz, OCH$_2$), 2.99 (m, 2H, CH$_2$), 2.87 (m, 3H, CH$_2$+OCH$_2$), 2.71 (m, 1H, CH), 1.93 (d, 2H, J=10.0 Hz, CH$_2$), 1.80 (m, 2H, CH$_2$), 1.52 (m, 7H, CH$_3$+CH$_2$), 1.24 (m, 2H, CH+CH), 0.87 (m, 12H, CH$_3$) ppm; ESI-MS: m/z=669 [M+H]$^+$.

Preparation Example 89. 4-(pyridin-2-yl carbamoyl) piperidin-1-oyl-Leu-Phe-Leu-epoxy ketone (5k)

By using 4-(pyridin-2-yl carbamoyl)piperidin-1-oyl-Leu (4k) as a raw material, the synthesis and post-treatment were carried out according to the same procedure as in Preparation Example 81. 0.45 g white solid was obtained with a yield of 70%. $^1$H NMR (500 MHz, CDCl$_3$): δ=8.65 (s, 1H, NH), 8.24 (m, 2H, pyridine-H), 7.75 (m, 1H, pyridine-H), 7.23 (m, 5H, Ar—H), 7.08 (dd, 1H, J=7.0, 1.5 Hz, pyridine-H), 6.93 (d, 1H, J=8.0 Hz, NH), 6.73 (d, 1H, J=8.0 Hz, NH), 4.84 (d, 1H, J=6.0 Hz, NH), 4.62 (q, 1H, J=7.0 Hz, CH), 4.56 (m, 1H, CH), 4.24 (m, 1H, CH), 3.93 (dd, 2H, J=35.0, 13.0 Hz, CH$_2$), 3.27 (d, 1H, J=5.0 Hz, OCH$_2$), 3.06 (m, 2H, CH$_2$), 2.85 (m, 3H, CH$_2$+OCH$_2$), 2.52 (m, 1H, CH), 1.92 (d, 2H, J=11.0 Hz, CH$_2$), 1.76 (m, 2H, CH$_2$), 1.60 (m, 2H, CH$_2$), 1.50 (m, 5H, CH$_3$+CH$_2$), 1.22 (m, 2H, CH+CH), 0.88 (m, 12H, CH$_3$) ppm; ESI-MS: m/z=663 [M+H]$^+$.

Preparation Example 90. 4-(pyridin-3-yl carbamoyl) piperidin-1-oyl-Leu-Phe-Leu-epoxy ketone (5l)

By using 4-(pyridin-2-yl carbamoyl)piperidin-1-oyl-Leu (4l) as a raw material, the synthesis and post-treatment were carried out according to the same procedure as in Preparation Example 81. 0.48 g white solid was obtained with a yield of 72%. $^1$H NMR (500 MHz, CDCl$_3$): δ=8.77 (m, 2H, pyridine-H+NH), 8.49 (d, 1H, J=8.0 Hz, pyridine-H), 8.32 (d, 1H, J=4.5 Hz, pyridine-H), 7.39 (dd, 1H, J=8.5, 5.0 Hz, pyridine-H), 7.22 (m, 5H, Ar—H), 6.97 (d, 1H, J=7.5 Hz, NH), 6.77 (d, 1H, J=7.5 Hz, NH), 5.02 (d, 1H, J=6.0 Hz, NH), 4.63 (q, 1H, J=7.0 Hz, CH), 4.53 (m, 1H, CH), 4.20 (m, 1H, CH), 3.96 (m, 2H, CH$_2$), 3.24 (d, 1H, J=5.0 Hz, OCH$_2$), 3.09 (m, 2H, CH$_2$), 2.85 (m, 3H, CH$_2$+OCH$_2$), 2.58 (m, 1H, CH), 1.94 (t, 2H, J=9.5 Hz, CH$_2$), 1.79 (m, 2H, CH$_2$), 1.58 (m, 2H, CH$_2$), 1.51 (m, 7H, CH$_3$+CH$_2$), 0.89 (m, 12H, CH$_3$) ppm; $^{13}$C NMR (125 MHz, CDCl$_3$): δ=208.08, 173.35, 173.29, 170.88, 157.16, 144.94, 141.19, 136.50, 135.26, 129.29, 128.56, 127.46, 126.98, 123.80, 58.99, 54.14, 53.56, 52.32, 50.13, 43.79, 43.57, 43.51, 41.00, 39.88, 37.53, 29.07, 28.26, 24.98, 24.93, 23.32, 22.92, 22.01, 21.31, 16.70; ESI-MS: m/z=663 [M+H]$^+$.

Preparation Example 91. 4-(4-chlorophenyl carbamoyl)piperazin-1-oyl-Leu-Phe-Leu-epoxy ketone (5m)

By using 4-(4-chlorophenyl carbamoyl)piperazin-1-oyl-Leu (4m) as a raw material, the synthesis and post-treatment were carried out according to the same procedure as in Preparation Example 81. 0.45 g white solid was obtained with a yield of 65%. $^1$H NMR (500 MHz, CDCl$_3$): δ=7.33 (d, 2H, J=8.0 Hz, Ar—H), 7.21 (m, 7H, Ar—H), 6.87 (brs, 1H, NH), 6.60 (m, 2H, NH), 5.03 (brs, 1H, NH), 4.61 (d, 1H, J=5.0 Hz, CH), 4.54 (m, 1H, CH), 4.25 (m, 1H, CH), 3.48 (m, 8H, CH$_2$), 3.22 (d, 1H, J=5.0 Hz, OCH$_2$), 3.05 (m, 2H, CH$_2$), 2.85 (d, 1H, J=5.0 Hz, OCH$_2$), 1.50 (m, 8H, CH+CH$_2$+CH$_3$), 1.21 (m, 1H, CH), 0.89 (m, 12H, CH$_3$) ppm; ESI-MS: m/z=697 [M+H]$^+$.

Preparation Example 92. 4-(4-methoxy phenyl carbamoyl)piperazin-1-oyl-Leu-Phe-Leu-epoxy ketone (5n)

By using 4-(4-methoxy phenyl carbamoyl)piperazin-1-oyl-Leu (4n) as a raw material, the synthesis and post-treatment were carried out according to the same procedure as in Preparation Example 81. 0.43 g white solid was obtained with a yield of 62%. $^1$H NMR (500 MHz, CDCl$_3$): δ=7.22 (m, 7H, Ar—H), 6.84 (m, 3H, Ar-H+NH), 6.56 (d, 1H, J=5.5 Hz, NH), 6.39 (brs, 1H, NH), 4.97 (brs, 1H, NH), 4.57 (m, 2H, CH+CH), 4.25 (m, 1H, CH), 3.78 (s, 3H, CH$_3$), 3.46 (m, 8H, CH$_2$), 3.24 (d, 1H, J=5.0 Hz, OCH$_2$), 3.05 (m, 2H, CH$_2$), 2.85 (d, 1H, J=5.0 Hz, OCH$_2$), 1.55 (m, 8H, CH+CH$_2$+CH$_3$), 1.24 (m, 1H, CH), 0.89 (m, 12H, CH$_3$) ppm; ESI-MS: m/z=693 [M+H]$^+$.

Preparation Example 93. 4-(4-chloro benzamido) piperidin-1-oyl-Leu-Phe-Leu-epoxy ketone (5o)

By using 4-(4-chloro benzamido)piperidin-1-oyl-Leu (4o) as a raw material, the synthesis and post-treatment were carried out according to the same procedure as in Preparation Example 81. 0.38 g white solid was obtained with a yield of 55%. $^1$H NMR (500 MHz, CDCl$_3$): δ=7.70 (d, 2H, J=8.5 Hz, Ar—H), 7.41 (d, 2H, J=8.5 Hz, Ar—H), 7.21 (m, 5H, Ar—H), 6.80 (brs, 1H, NH), 6.50 (d, 1H, J=7.0 Hz, NH), 6.15 (d, 1H, J=5.0 Hz, NH), 4.81 (brs, 1H, NH), 4.61 (m, 1H, CH), 4.52 (m, 1H, CH), 4.17 (m, 2H, CH+CH), 3.90 (m, 2H, CH$_2$), 3.19 (d, 1H, J=5.0 Hz, OCH$_2$), 3.05 (m, 2H, CH$_2$), 2.93 (m, 2H, CH$_2$), 2.82 (d, 1H, J=5.0 Hz, OCH$_2$), 2.03 (m, 2H, CH$_2$), 1.69 (m, 2H, CH$_2$), 1.49 (m, 8H, CH+CH$_2$+CH$_3$), 1.23 (m, 1H, CH), 0.90 (m, 12H, CH$_3$) ppm; ESI-MS: m/z=696 [M+H]$^+$.

Preparation Example 94. 4-(4-methoxy benzamido) piperidin-1-oyl-Leu-Phe-Leu-epoxy ketone (5p)

By using 4-(4-methoxy benzamido)piperidin-1-oyl-Leu (4p) as a raw material, the synthesis and post-treatment were carried out according to the same procedure as in Preparation Example 81. 0.45 g white solid was obtained with a yield of 65%. $^1$H NMR (500 MHz, CDCl$_3$): δ=7.72 (d, 2H, J=8.5 Hz, Ar—H), 7.24 (m, 5H, Ar—H), 6.92 (d, 2H, J=8.5 Hz, Ar—H), 6.82 (brs, 1H, NH), 6.53 (d, 1H, J=8.0 Hz, NH), 6.01 (d, 1H, J=7.0 Hz, NH), 4.80 (brs, 1H, NH), 4.62 (q, 1H, J=7.0 Hz, CH), 4.53 (m, 1H, CH), 4.19 (m, 2H, CH+CH), 3.87 (m, 5H, CH$_3$+CH$_2$), 3.23 (d, 1H, J=5.0 Hz, OCH$_2$), 3.08 (m, 2H, CH$_2$), 2.92 (m, 2H, CH$_2$), 2.83 (d, 1H, J=5.0 Hz, OCH$_2$), 2.04 (m, 2H, CH$_2$), 1.65 (m, 2H, CH$_2$), 1.50 (m, 8H, CH+CH$_2$+CH$_3$), 1.25 (m, 1H, CH), 0.90 (m, 12H, CH$_3$) ppm; ESI-MS: m/z=692 [M+H]$^+$.

Preparation Example 95. 4-(morpholin-4-oyl)piperidin-1-oyl-Leu-Phe-Leu-epoxy ketone (5q)

By using 4-(morpholin-4-oyl)piperidin-1-oyl-Leu (4q) as a raw material, the synthesis and post-treatment were carried out according to the same procedure as in Preparation Example 81. 0.38 g white solid was obtained with a yield of 58%. $^1$H NMR (500 MHz, CDCl$_3$): δ=7.22 (m, 5H, Ar—H), 6.83 (d, 1H, J=8.0 Hz, NH), 6.58 (d, 1H, J=8.0 Hz, NH), 4.78 (d, 1H, J=6.5 Hz, NH), 4.57 (m, 2H, CH+CH), 4.20 (m, 1H, CH), 3.91 (m, 2H, CH$_2$), 3.68 (m, 4H, CH$_2$), 3.62 (m, 2H, CH$_2$), 3.51 (m, 2H, CH$_2$), 3.28 (d, 1H, J=5.0 Hz, OCH$_2$), 3.06 (m, 2H, CH$_2$), 2.83 (m, 3H, OCH$_2$+CH$_2$), 2.62 (m, 1H, CH), 1.72 (m, 4H, CH$_2$), 1.51 (m, 7H, CH$_3$+CH$_2$), 1.22 (m, 2H, CH+CH), 0.89 (m, 12H, CH$_3$) ppm; ESI-MS: m/z=656 [M+H]$^+$.

Preparation Example 96. 3-(pyrazin-2-yl carbamoyl)piperidin-1-oyl-Leu-Phe-Leu-epoxy ketone (5r)

By using 3-(pyrazin-2-yl carbamoyl)piperidin-1-oyl-Leu (4r) as a raw material, the synthesis and post-treatment were carried out according to the same procedure as in Preparation Example 81. 0.34 g white solid was obtained with a yield of 52%. $^1$H NMR (500 MHz, CDCl$_3$): δ=9.52 and 9.50 (s, 1H, 50/50, pyrazine-H), 9.27 (m, 1H, NH), 8.33 (m, 1H, pyrazine-H), 8.25 and 8.23 (s, 1H, 50/50, pyrazine-H), 7.18 (m, 5H, Ar—H), 6.78 and 6.55 (brs, 1H, 50/50, NH), 5.29 (m, 1H, NH), 4.60 (m, 2H, CH+NH), 4.33 (m, 1H, CH), 4.07 (m, 1H, CH), 3.81 and 3.59 (m, 1H, CH$_2$), 3.15 (m, 5H, OCH$_2$+CH$_2$), 2.85 (d, 1H, J=6.0 Hz, OCH$_2$), 2.66 (m, 1H, CH), 2.01 (m, 5H, CH$_2$), 1.48 (m, 8H, CH+CH$_2$+CH$_3$), 1.21 (m, 1H, CH), 0.87 (m, 12H, CH$_3$) ppm; ESI-MS: m/z=664 [M+H]$^+$.

Preparation Example 97. 3-(4-chlorophenyl carbamoyl)piperidin-1-oyl-Leu-Phe-Leu-epoxy ketone (5s)

By using 3-(4-chlorophenyl carbamoyl)piperidin-1-oyl-Leu (4s) as a raw material, the synthesis and post-treatment were carried out according to the same procedure as in Preparation Example 81. 0.31 g white solid was obtained with a yield of 45%. $^1$H NMR (500 MHz, CDCl$_3$): δ=9.03 and 8.98 (s, 1H, 50/50, NH), 7.56 (m, 2H, Ar—H), 7.21 (m, 7H, Ar—H), 6.59 and 5.36 (brs, 1H, 50/50, NH), 6.47 and 5.07 (d, 1H, 50/50, J=8.0 Hz, NH), 4.55 (m, 2H, CH+NH), 4.32 (m, 1H, CH), 3.72 (m, 2H, CH+CH$_2$), 3.12 (m, 5H, OCH$_2$+CH$_2$), 2.83 and 2.77 (d, 1H, 50/50, J=5.0 Hz, OCH$_2$), 2.51 (m, 1H, CH), 2.02 (m, 5H, CH$_2$), 1.52 (m, 8H, CH+CH$_2$+CH$_3$), 1.22 (m, 1H, CH), 0.87 (m, 12H, CH$_3$) ppm; ESI-MS: m/z=696 [M+H]$^+$.

Preparation Example 98. 4-(pyrazin-2-yl carbamoyl)piperidin-1-oyl-Leu-Phe-Leu-cyclothione (5t)

The yield was 56%. ESI-MS: m/z=680.8811 [M+H]$^+$

Preparation Example 99. 4-(4-fluorophenyl carbamoyl)piperidin-1-oyl-Leu-Phe-Leu-cyclothione (5u)

The yield was 71%. ESI-MS: m/z=696.8941 [M+H]$^+$

Preparation Example 100. 4-(pyrazin-2-yl carbamoyl)piperidin-1-oyl-Leu-Phe-Leu-aziridinone (5v)

The yield was 61%. ESI-MS: m/z=663.8312 [M+H]$^+$

Preparation Example 101. 4-(pyrazin-2-yl carbamoyl)piperidin-1-oyl-Leu-Phe-Leu-(N-ethyl aziridinone) (5v)

The yield was 67%. ESI-MS: m/z=691.8832 [M+H]$^+$

Test Example 1. Test of Proteasome Inhibitory Activity of the Tripeptide Epoxy Ketone Compounds Constructed with a Heterocycle Experimental Method: By using a fluorescent substrate Suc-Leu-Leu-Val-Tyr-AMC to observe the inhibition of various compounds on activity of the enzyme, the inhibitory effect of the compounds was preliminarily evaluated. Human proteasome chymotrypsin-like protease may hydrolyze the sequence Tyr-AMC of the substrate to release AMC. The fluorescent absorption of AMC as the hydrolytic product can be detected under the condition of an excitation light of 355 nm and an emission light of 460 nm such that the inhibition of the compounds on activity of the enzyme may be observed. Results are shown in Table 1.

TABLE 1

Inhibitory activity of compounds on proteasome CT-L and proliferation inhibitory activity thereof on multiple myeloma cells

| Compound | Proteasome CT-L Inhibition, IC$_{50}$ (nM) | Cytotoxicity IC$_{50}$ (nM) | |
|---|---|---|---|
| | | RPMI8226 cell | NCI-H929 cell |
| 5a | 40.1 | 16.6 | 40.4% @100 nM |
| 5b | 6.5 | 8.0 | 60.0 |
| 5c | 90.8 | 28.9 | 100.5 |
| 5d | 3.4 | 6.7 | 38.2 |
| 5e | 2.4 | 4.3 | 46.5 |
| 5f | 9.4 | 9.0 | 75.8 |
| 5g | 4.6 | 4.7 | 35.6 |
| 5h | 4.8 | 4.7 | 33.7 |
| 5i | 6.4 | 9.5 | 49.2 |
| 5j | 1.5 | 3.2 | 33.4 |
| 5k | 1.5 | 2.5 | 15.3 |
| 5l | 3.6 | 7.7 | 41.7 |
| 5m | 25.6 | 3.0 | 6.4 |
| 5n | 31.7 | 4.3 | 3.8 |
| 5o | 14.5 | 2.4 | 4.1 |
| 5p | 24.1 | 1.2 | 5.0 |
| 5q | 484.1 | NT | NT |
| 5r | 355.2 | 19.2 | 73.6 |
| 5s | 782.7 | 83.9 | 154.1 |
| 5t | >1000 | >1000 | >1000 |
| 5u | >1000 | >1000 | >1000 |
| 5v | >1000 | >1000 | >1000 |
| 5w | >1000 | >1000 | >1000 |
| Bortezomib | 10.8 | 1.8 | 9.5 |
| Carfilzomib | 8.6 | 3.0 | 28.8 |

Note:
NT—no tests.

Test Example 2. Test of Proliferation Inhibitory Activity of the Tripeptide Epoxy Ketone Compounds Constructed with a Heterocycle on Multiple Myeloma Cells Experimental Method: Cell viability was determined by MTT method preformed as follows. Cells grown at the logarithmic growth phase was digested with a 0.01% trypsin, counted, plated in a 96-cell plate at a cell density of 2.0*10³/well for 100 ml, and cultured in a 5% $CO_2$ incubator at a temperature of 37° C. overnight. For each of the compounds, a gradient of six concentrations were set, in triplicate for each concentration. Compounds of each concentration were added to the corresponding cell, respectively, and cultured in a 5% $CO_2$ incubator at a temperature of 37° C. for 72 h. 20 ml of 5 mg/ml MTT was added to each of the cells. After incubation at a temperature of 37° C. for 3 h, supernatant was removed by suction. 100 ml of DMSO was added for dissolution. Absorption at 550 nm (L1) was determined by using SpectraMAX 340 with a reference wavelength of 690 nm (L2). The values of (L1-L2) were plotted against various concentrations, and fitted into a formula to give $IC_{50}$. The results are shown in Table 1.

Test Example 3. Test of Proliferation Inhibitory Activity of Part of the Tripeptide Epoxy Ketone Compounds Constructed with a Heterocycle on Various Tumor Cells The experimental method may be referred to Test Example 2, except that the cell strains of RPMI8226 and NCI-H929 were replaced with corresponding tumor cells. The results are shown in Table 2.

TABLE 2

Proliferation inhibitory activities of part of the compounds on various tumor cells

| Cell line | Compound |  |  |  |
|---|---|---|---|---|
|  | 5j | 5k | 5l | Carfilzomib |
|  | $IC_{50}$ (nM) |  |  |  |
| LP1 | 12.67 ± 3.66 | 15.20 ± 2.82 | 80.64 ± 17.79 | 22.74 ± 2.51 |
| MGC-803 | 4.91 ± 0.21 | 3.72 ± 0.13 | 19.20 ± 1.72 | 8.95 ± 0.12 |
|  | $IC_{50}$ (μM) |  |  |  |
| HCT116 | 9.77 ± 0.81 | 5.72 ± 0.72 | 75.45 ± 9.08 | 8.93 ± 1.44 |
| PC-3 | 11.72 ± 1.35 | 7.74 ± 0.77 | 62.24 ± 5.28 | 24.18 ± 2.72 |
| MCF-7 | 0.24 ± 0.03 | 0.42 ± 0.04 | 1.12 ± 0.09 | 1.02 ± 0.07 |
|  | Cell activity (%) |  |  |  |
| BORT (1 μM) | 52.75 ± 2.54 | 54.48 ± 2.13 | 63.51 ± 2.88 | 61.08 ± 2.49 |
| HELA (10 μM) | 54.33 ± 2.06 | 55.84 ± 3.53 | 60.67 ± 4.24 | 61.21 ± 3.44 |
| K562 (10 μM) | 53.62 ± 1.62 | 55.58 ± 1.53 | 52.45 ± 1.58 | 58.56 ± 1.04 |
| MM-1R (100 nM) | 82.19 ± 2.36 | 88.19 ± 7.24 | 90.24 ± 4.65 | 92.15 ± 6.34 |
| MM-1S (100 nM) | 67.34 ± 2.48 | 72.22 ± 3.19 | 71.73 ± 3.53 | 76.22 ± 1.36 |

Test Example 4. Selectivity Assay of Part of Tripeptide Epoxy Ketone Compounds Constructed with a Heterocycle for Three Hydrolytic Active Sites of Proteasome The experimental method may be referred to Test Example 1, except that the substrates in tests for inhibitory activities of PGPH and T-L were replaced with Z-Leu-Leu-Glu-AMC and Bz-Val-Gly-Arg-AMC, respectively. The results are shown in Table 3.

TABLE 3

Inhibitory activity and selectivity of part of the compounds for three active sites of proteasome

| Compound | $IC_{50}$ (nM) |  |  |
|---|---|---|---|
|  | CT-L | PGHP (Fold/CT-L) | T-L (Fold/CT-L) |
| 5j | 1.5 ± 0.2 | 421.8 ± 13.6 (281.2) | 2428.3 ± 130.2 (1618.8) |
| 5k | 1.5 ± 0.2 | 484.7 ± 26.1 (321.0) | 3181.5 ± 47.2 (2107.0) |
| 5l | 3.6 ± 0.5 | 461.8 ± 27.2 (127.6) | 2869.2 ± 381.1 (792.6) |
| Bortezomib | 10.8 ± 0.9 | 113.5 ± 6.8 (10.5) | 8832.7 ± 189.9 (817.8) |
| Carfilzomib | 8.6 ± 1.4 | 610.2 ± 37.7 (76.3) | 586.9 ± 31.4 (68.3) |

Test Example 5. Inhibitory Activity of Part of Tripeptide Epoxy Ketone Compounds Constructed with a Heterocycle on Hemocyte Proteasome CT-L Experimental Method: An anticoagulant was added to the blood taken from ICR mice. Subsequently, the compound of a final concentration of 1.25 μg/mL was added (volume ratio of the compound to the blood was 1:50). After incubation for 40 min, the sample was centrifuged (1000 rpm, 5 min), and the supernatant was removed. A 2-fold volume of EDTA (5 mM, pH=8.0) was added for lysis. The blood sample was rotated in a 4° C. rotator for 60 min, and then centrifuged (6600 rpm, 10 min) to remove the sediment at the bottom. The protein concentration of the lysated blood sample was determined. After calibrating to the same protein concentration, proteasome activity was tested. The test method was the same as in Test Example 1. The results are shown in FIG. 1.

Test Example 6. Test of Inhibitory Activity of Part of Tripeptide Epoxy Ketone Compounds Constructed with a Heterocycle on Normal Mouse Acute Proteasome Experimental Method: Normal ICR mice were administered intravenously at a dosage of 1 mg/kg. Carfilzomib was used as a positive control, and physiological saline was used as a blank control. At 24 h after administration, blood was taken from mice's orbital venous plexus. Equal volume of physiological saline was added to the blood sample for centrifugation (1000 rpm, 5 min). The supernatant was discarded. A 2-fold volume of EDTA (5 mM, pH=8.0) was added for lysis. The blood sample was rotated in a 4° C. rotator for 60 min, and then centrifuged (6600 rpm, 10 min) to remove the sediment at the bottom. The protein concentration of the lysated blood sample was determined. After calibrating to the same protein concentration, proteasome activity was tested. The test method was the same as in Test Example 1.

Figure 2:
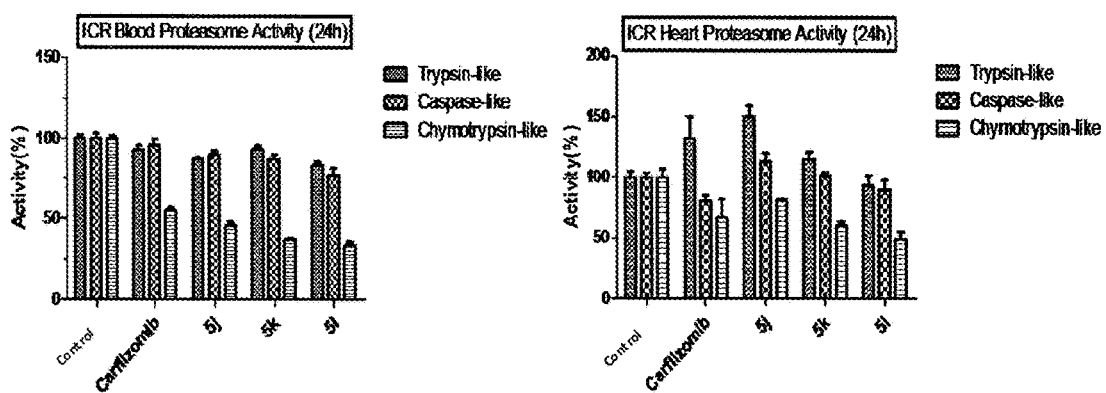
FIG. 2 shows the inhibitory activity of part of the compounds on the proteasome in hemocytes and heart tissues of normal mice.

After taking the blood sample from orbit, the mice were dissected, and the heart was taken out. Meanwhile, the blood in the heart was removed, and then the heart was homogenated and centrifuged (6600 rpm, 10 min). The protein concentration was determined. After calibrating to the same protein concentration, heart proteasome activity was tested. The test method was the same as in Test Example 1. The results are shown in FIG. 2.

Test Example 7. Test of Proteasome Inhibitory Activity of Part of Tripeptide Epoxy Ketone Compounds Constructed with a Heterocycle on NOD/SCID Tumor-Bearing Mice Experimental Method: Human myeloma RPMI8226 cell strain was inoculated subcutaneously at right flank of NOD/

SCID mice with an inoculation quantity of 1×10⁷ cells/mouse. After forming a xenograft, the experiment was started.

Tumor-bearing NOD/SCID mice inoculated with RPMI 8226 tumor cells were divided into four groups by weight randomly with 4 mice per group. Each of the groups was administered intravenously at a dosage of 5 mg/kg. Carfilzomib was used as a positive control, and physiological saline was used as a blank control. At 1 h and 24 h after administration, blood was taken from mice's orbital venous plexus, respectively. Equal volume of physiological saline was added to the blood sample for centrifugation (1000 rpm, 5 min). The supernatant was discarded. A 2-fold volume of EDTA (5 mM, pH=8.0) was added for lysis. The blood sample was rotated in a 4° C. rotator for 60 min, and then centrifuged (6600 rpm, 10 min) to remove the sediment at the bottom. The protein concentration of the lysated blood sample was determined. After calibrating to the same protein concentration, proteasome activity was assayed.

Figure 3:
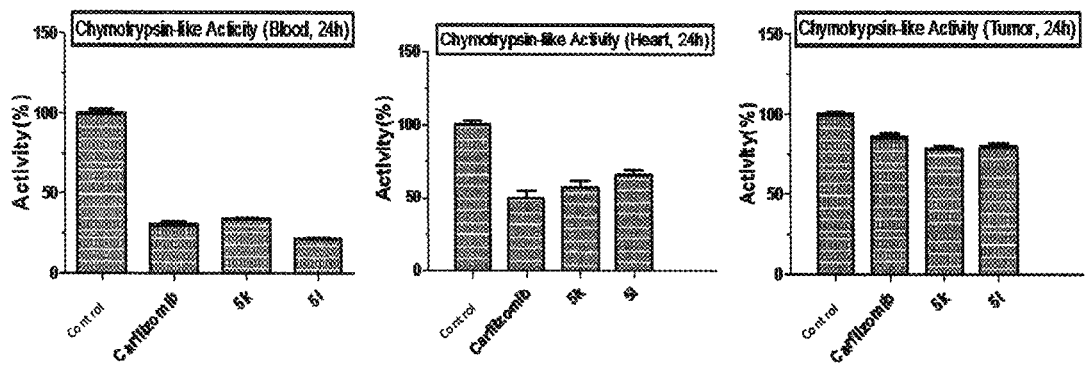
FIG. 3 shows the inhibitory activity of part of the compounds on the proteasome CT-L in blood and tissues of tumor-bearing mice.

After taking the blood sample at two time points of 1 h and 24 h, the mice were dissected, and the heart, liver and tumor tissue were taken out. After grinding, the tissues were homogenated and centrifuged (6600 rpm, 10 min). The protein concentration was determined. After calibrating to the same protein concentration, the tissue proteasome activities were assayed. The results are shown in FIG. 3.

Test Example 8. Test of Growth Inhibitory Activity of Part of Tripeptide Epoxy Ketone Compounds Constructed with a Heterocycle on Subcutaneous Xenograft of Human Myeloma RPMI 8226 NOD/SCID Mice Experimental Method: Human myeloma RPMI8226 cell strain was inoculated subcutaneously at right flank of NOD/SCID mice with an inoculation quantity of 1×10⁷ cells/mouse. After forming a xenograft, the experiment was started.

Figure 4:
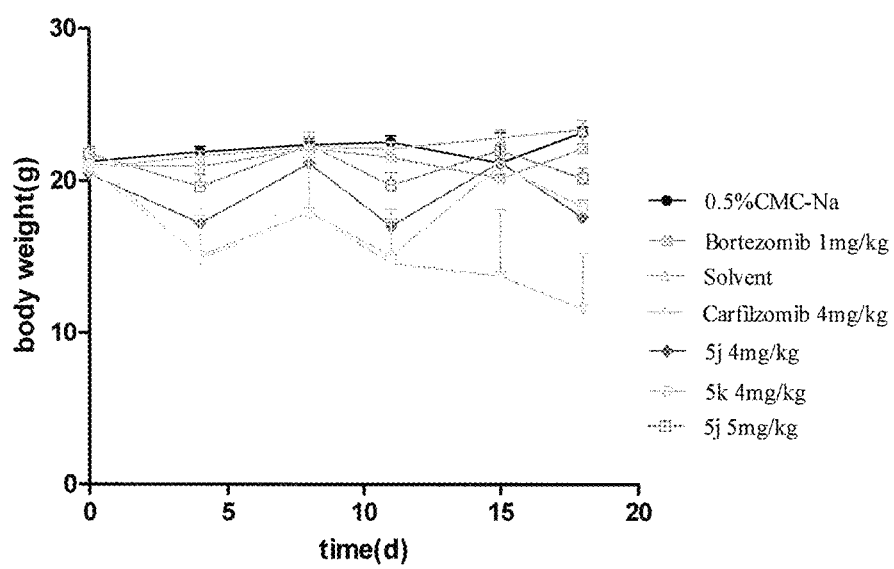
FIG. 4 shows the effect of the compounds on body weight of human myeloma RPMI 8226 NOD/SCID mice.

The diameters of subcutaneous xenografts of NOD/SCID mice were measured with a vernier caliper. After the tumor was grown to the size of 100-300 mm³, the animals were grouped randomly. Equal volume of blank solvent was administered to the group of solvent control. During the experimentation, the diameters of subcutaneous xenografts were measured twice a week, and the mice were weighed at the same time. Results are shown in Table 4 and FIG. 4.

The present compounds are efficient inhibitors of proteasome. As shown in results of activity assays, proteasome inhibitory activities of eight compounds are superior over commercially available compounds Bortezomib and Carfilzomib, exhibiting extremely strong proliferation inhibitory activity against multiple myeloma cells. In further study of proteasome activity of blood and tissues of normal mice, it has been found that three compounds have better or comparable activity versus the positive control. Furthermore, the compounds have a good selectivity for three hydrolytic active sites of proteasome. Among the compounds, two compounds not only have good inhibitory effect on proteasomes of blood and tissues of tumor-bearing mice, but also exhibit a significant inhibitory effect on human myeloma mice xenograft, with a better tumor inhibition than that of the positive control and no significant effect on weights of mice. The above experiments have demonstrated that the present compounds have an excellent prospective of antitumor application, and thereby have a good commercial value.

What is claimed is:

1. A tripeptide epoxy ketone compound having the following structural formula,

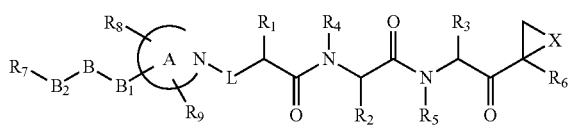

or a salt thereof, wherein:

$R_1$, $R_2$ and $R_3$ are each independently selected from the group consisting of $C_{1-6}$ alkyl and aralkyl;

$R_4$ and $R_5$ are each independently H;

$R_6$ is selected from the group consisting of H and $C_{1-6}$ alkyl;

X is selected from the group consisting of O, S, NH and N—$C_{1-6}$ alkyl;

L is

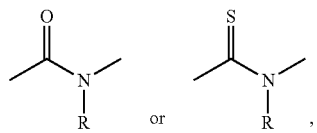

TABLE 4

Effect of compounds on tumor weights of xenografts of human myeloma RPMI8226 NOD/SCID mice

| group | Tumor weight (g) | | | | | | | Tumor inhibition (%) |
| --- | --- | --- | --- | --- | --- | --- | --- | --- |
| | 1 | 2 | 3 | 4 | 5 | 6 | mean ± SD | |
| 0.5% CMC-Na | 1.11 | 1.20 | 1.43 | 0.88 | 1.43 | 1.79 | 1.27 ± 0.25 | — |
| | 0.87 | 1.33 | 1.07 | 1.39 | 1.19 | 1.49 | | |
| Bortezomib (1 mg/kg) | 1.21 | 0.38 | 0.92 | 0.90 | 0.74 | 0.80 | 0.83 ± 0.25* | 34.78 |
| Solvent | 0.62 | 1.49 | 1.91 | 1.02 | 1.29 | 1.17 | 1.25 ± 0.41 | 1.19 |
| Carfilzomib (4 mg/kg) | 0.57 | — | — | 0.38 | 0.32 | 0.85 | 0.53 ± 0.21* | 58.10 |
| 5j (4 mg/kg) | 0.52 | 0.53 | 0.52 | 0.99 | 0.29 | 0.61 | 0.58 ± 0.21* | 54.41 |
| 5k (4 mg/kg) | 0.20 | 0.66 | 0.44 | 0.52 | 0.72 | 0.98 | 0.59 ± 0.24* | 53.62 |
| 5l (5 mg/kg) | 0.53 | 0.54 | 0.30 | 0.40 | 0.63 | 0.21 | 0.44 ± 0.15* | 65.61 |

P value vs 0.5% CMC-Na group,
*p < 0.01 where R is H;

the ring A is a 5-7 membered saturated aliphatic heterocycle;

$R_8$ and $R_9$ are each H;

$B_1$ and $B_2$ are the same or different, and are each independently $N(R_c)$, or are absent, where $R_c$ is selected from the group consisting of H and $C_{1-6}$ alkyl;

B is selected from the group consisting of

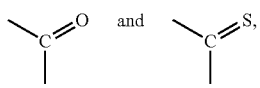

and $R_7$ is selected from the group consisting of heterocyclic group, aryl and heteroaryl, wherein aryl is optionally substituted by halogen or $C_{1-6}$ alkoxy group.

2. The compound according to claim 1, wherein: X is O.

3. The compound according to claim 1, selected from the following compounds:

4-(pyrazin-2-yl carbamoyl)piperidin-1-oyl-Phe-Leu-Leu-epoxy ketone;
1-(pyrazin-2-oyl)piperidin-4-oyl-Phe-Leu-Leu-epoxy ketone;
4-(pyrazin-2-yl carbamoyl)piperidin-1-oyl-Leu-Phe-Leu-epoxy ketone;
1-(pyrazin-2-oyl)piperidin-4-oyl-Leu-Phe-Leu-epoxy ketone;
4-(pyrazin-2-oyl)piperazin-1-oyl-Leu-Phe-Leu-epoxy ketone;
4-(pyrazin-2-formamido)piperidin-1-oyl-Leu-Phe-Leu-epoxy ketone;
4-(4-fluorophenyl carbamoyl)piperidin-1-oyl-Leu-Phe-Leu-epoxy ketone;
4-(4-benzoyl phenyl carbamoyl)piperidin-1-oyl-Leu-Phe-Leu-epoxy ketone;
4-(biphenyl-4-yl carbamoyl)piperidin-1-oyl-Leu-Phe-Leu-epoxy ketone;
4-(4-chlorophenyl carbamoyl)piperidin-1-oyl-Leu-Phe-Leu-epoxy ketone;
4-(4-methoxy phenyl carbamoyl)piperidin-1-oyl-Leu-Phe-Leu-epoxy ketone;
4-(isoxazol-3-yl carbamoyl)piperidin-1-oyl-Leu-Phe-Leu-epoxy ketone;
4-(thiazol-2-yl carbamoyl)piperidin-1-oyl-Leu-Phe-Leu-epoxy ketone;
4-(1,3,4-thiadiazol-2-yl carbamoyl)piperidin-1-oyl-Leu-Phe-Leu-epoxy ketone;
4-(benzo[d]thiazol-2-yl carbamoyl)piperidin-1-oyl-Leu-Phe-Leu-epoxy ketone;
4-(pyridin-2-yl carbamoyl)piperidin-1-oyl-Leu-Phe-Leu-epoxy ketone;
4-(pyridin-3-yl carbamoyl)piperidin-1-oyl-Leu-Phe-Leu-epoxy ketone;
4-(pyridin-4-yl carbamoyl)piperidin-1-oyl-Leu-Phe-Leu-epoxy ketone;
4-(pyrimidin-2-yl carbamoyl)piperidin-1-oyl-Leu-Phe-Leu-epoxy ketone;
1-(4-chlorophenyl carbamoyl)piperidin-4-oyl-Leu-Phe-Leu-epoxy ketone;
1-(4-methoxy phenyl carbamoyl)piperidin-4-oyl-Leu-Phe-Leu-epoxy ketone;
4-(4-chlorophenyl carbamoyl)piperazin-1-oyl-Leu-Phe-Leu-epoxy ketone;
4-(4-methoxy phenyl carbamoyl)piperazin-1-oyl-Leu-Phe-Leu-epoxy ketone;
4-(4-chloro benzamido)piperidin-1-oyl-Leu-Phe-Leu-epoxy ketone;
4-(4-methoxy benzamido)piperidin-1-oyl-Leu-Phe-Leu-epoxy ketone;
4-(4-chlorophenyl uramido)piperidin-1-oyl-Leu-Phe-Leu-epoxy ketone;
4-(4-methoxy phenyl uramido)piperidin-1-oyl-Leu-Phe-Leu-epoxy ketone;
3-(pyrazin-2-yl carbamoyl)piperidin-1-oyl-Leu-Phe-Leu-epoxy ketone;
3-(4-chlorophenyl carbamoyl)piperidin-1-oyl-Leu-Phe-Leu-epoxy ketone;
3-(4-methoxy phenyl carbamoyl)piperidin-1-oyl-Leu-Phe-Leu-epoxy ketone;
4-(morpholin-4-oyl)piperidin-1-oyl-Leu-Phe-Leu-epoxy ketone;
4-(2-morpholinyl ethyl carbamoyl)piperidin-1-oyl-Leu-Phe-Leu-epoxy ketone;
4-(2-hydroxy ethyl carbamoyl)piperidin-1-oyl-Leu-Phe-Leu-epoxy ketone;
4-(pyrazin-2-yl carbamoyl)piperidin-1-oyl-Leu-Phe-Leu-cyclothione;
4-(4-fluorophenyl carbamoyl)piperidin-1-oyl-Leu-Phe-Leu-cyclothione;
4-(pyrazin-2-yl carbamoyl)piperidin-1-oyl-Leu-Phe-Leu-aziridinone; or
4-(pyrazin-2-yl carbamoyl)piperidin-1-oyl-Leu-Phe-Leu-(N-ethyl aziridinone).

4. The compound according to claim 1, wherein the ring A is a six membered saturated aliphatic heterocycle.

5. The compound according to claim 1, wherein the ring A is piperidine or piperazine.

6. The compound according to claim 1, wherein $R_1$, $R_2$ and $R_3$ are each independently benzyl or isobutyl.

7. The compound according to claim 1, wherein $R_6$ is methyl.

8. The compound according to claim 1, wherein X is O, S, NH or N—$C_2H_5$.

9. The compound according to claim 1, wherein L is

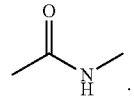

10. The compound according to claim 1, wherein $B_1$ and $B_2$ are the same or different, and are each independently NH, N—$C_2H_5$ or are absent.

11. The compound according to claim 1, wherein B is

12. The compound according to claim 1, wherein $R_7$ is pyrazine, benzoyl phenyl, biphenyl, isoxazole, thiazole, thiadiazole, benzothiazole, pyridine, morpholine, 4-chlorophenyl, 4-fluorophenyl, 4-methoxy phenyl or hydroxy.

13. The compound according to claim 1, wherein $B_1$, $B_2$, B and $R_7$ are taken together to form

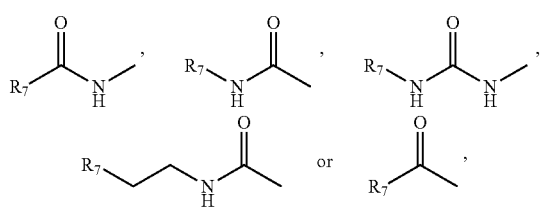

wherein $R_7$ is selected from the group consisting of heterocyclic group, aryl and heteroaryl, wherein aryl is optionally substituted by halogen or $C_{1-6}$ alkoxy group.

14. The compound according to claim 1, wherein:
$R_1$, $R_2$ and $R_3$ are each independently benzyl or isobutyl;
$R_6$ is methyl;
X is O, S, NH or N—$C_2H_5$;
L is

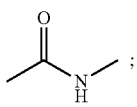

A is piperidine or piperazine; and
$B_1$, $B_2$, B and $R_7$ are taken together to form

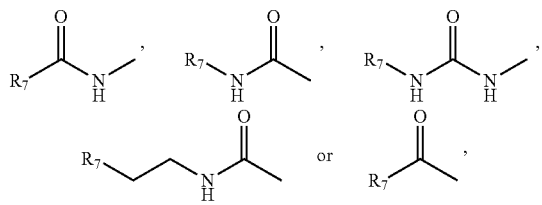

wherein $R_7$ is pyrazine, benzoyl phenyl, biphenyl, isoxazole, thiazole, thiadiazole, benzothiazole, pyridine, morpholine, 4-chlorophenyl, 4-fluorophenyl, 4-methoxy phenyl or hydroxy.

15. A pharmaceutical composition, comprising at least one compound according to claim 1 and one or more pharmaceutically acceptable carriers or excipients.

16. A method for treating a cancer, the method comprising administering a compound according to claim 1 to a subject having a cancerous tumor, wherein the cancerous tumor is a hematological tumor selected from the group consisting of myeloma, lymphoma, leukemia, breast cancer, prostate cancer, colon cancer, cervical cancer or gastric cancer.

17. The method according to claim 16, wherein the administering the compound to the subject comprises administering by oral, injection, inhalation, or implantation.

18. A method for preparing a tripeptide epoxy ketone compound, comprising the steps of:
(1) reacting a compound 6 with a protected amino acid for 2-8 h under the action of a condensing agent at a reaction temperature of 0-50° C. to give a compound 7 as a crude product to be used directly in the next step, wherein the condensing agent is selected from the group consisting of dicyclohexyl carbodiimide/4-dimethyl amino pyridine, dicyclohexyl carbodiimide/1-hydroxy benzotriazole, and N-(3-dimethyl amino propyl)-N'-ethyl carbodiimide hydrochloride/1-hydroxy benzotriazole, (2) deprotecting the Boc protective group off the compound 7 for 0.5-3 h in an acidic condition at a reaction temperature of −10 to 40° C. to give a crude product to be used directly in the next step, wherein the acidic condition is in the presence of a solution of HCl in ether, a solution of HCl in ethyl acetate, a solution of HCl in methanol, a solution of HCl in dioxane, or trifluoroacetic acid, (3) deprotecting the Boc protective group off the compound 1 in an acidic condition same as the reaction condition in the step of (2) to give a compound 2 as a crude product to be used directly in the next step, (4) reacting an amino acid methyl ester with triphosgene for 10 min to 1 h in a basic condition in the presence of sodium carbonate, sodium bicarbonate, triethylamine or diisopropylethylamine at a reaction temperature of −20 to 0° C. to give amino acid methyl ester isocyanate, and condensing the isocyanate with the compound 2 in a basic condition in the presence of triethylamine or diisopropyl ethylamine at a reaction temperature of 0-50° C. for 1-6 h to give a compound 3 as a crude product to be used directly in the next step, (5) hydrolyzing the compound 3 in a basic condition in the presence of sodium hydroxide, lithium hydroxide or potassium hydroxide under a reaction temperature of 0-40° C. for 0.5-2 h to give a compound 4 as a product to be used directly in the next step, (6) reacting the compound 4 with a compound 8 under the action of the same condensing agent as that in the step of (1) to give a product 5, and isolating the resultant crude product through column chromatography to give a pure product, Reaction Scheme:

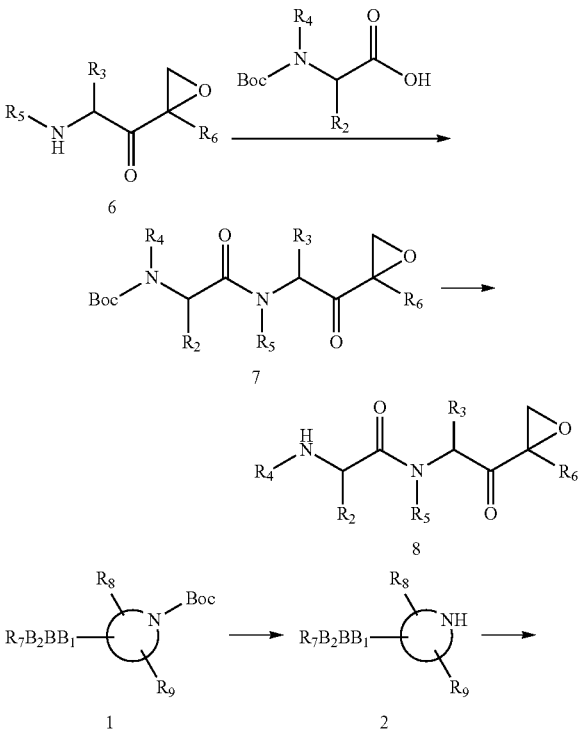

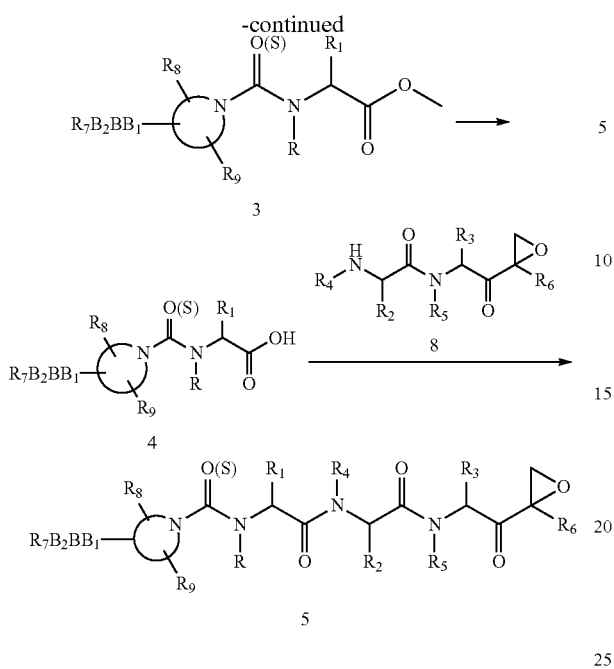
wherein $R_1$, $R_2$, $R_3$, $R_4$, $R_5$, $R_6$, $R_7$, $R_8$, $R_9$, B, $B_1$, $B_2$ and the shown ring are as defined in claim 1.
* * * * *